(12) United States Patent
Deininger et al.

(10) Patent No.: US 6,544,730 B1
(45) Date of Patent: Apr. 8, 2003

(54) HIGH DENSITY POLYMORPHIC GENETIC LOCUS

(76) Inventors: Prescott Deininger, 1300 Lark St., New Orleans, LA (US) 70122; David Kass, 2417 Burns Ave., Ypsilanti, MI (US) 48197

( * ) Notice: Subject to any disclaimer, the term of this patent is extended or adjusted under 35 U.S.C. 154(b) by 623 days.

(21) Appl. No.: 08/958,009

(22) Filed: Oct. 27, 1997

(51) Int. Cl.[7] ............. C12Q 1/68; C12P 19/34; C07H 21/02
(52) U.S. Cl. ............. 435/6; 435/91.1; 435/91.2; 536/23.1; 536/24.3; 536/24.31; 536/24.33
(58) Field of Search .......... 435/6, 91.1, 91.2; 536/23.1, 24.3, 24.31, 24.33

(56) References Cited

U.S. PATENT DOCUMENTS

| | | |
|---|---|---|
| 5,032,501 A | 7/1991 | Milner |
| 5,075,217 A | 12/1991 | Weber |
| 5,175,082 A | 12/1992 | Jeffreys |
| 5,192,658 A | 3/1993 | Loewy et al. |
| 5,310,893 A | 5/1994 | Erlich et al. |
| 5,369,004 A | 11/1994 | Polymeropoulos |
| 5,378,602 A | 1/1995 | Polymeropoulos |
| 5,468,610 A | 11/1995 | Polymeropoulos |
| 5,514,547 A | 5/1996 | Balasz et al. |
| 5,541,065 A | 7/1996 | Erlich et al. |
| 5,582,979 A | 12/1996 | Weber |

OTHER PUBLICATIONS

Yamamoto et al, "The human LDL receptor: A cysteine rich protein with multiple Alu sequences in its mRNA", Cell 39:27–38, Nov. 1984.*

Cotton et al, "Detection of mutations in DNA", Current Opinion in Biotechnology 3:24–30, 1992.*

Kass, D.H., M.A. Batzer, et al (1995). "A new restriction–site polymorphism in exon 18 of the low density lipoprotein receptor (LDLR) gene." Hum Genet 95:363–364.

Kass, D.H., M.A. Batzer, et al(1995). "Gene conversion as a secondary mechanism of short interspersed element (SINE) evolution." Mol Cell Biol 15:19–25.

Batzer, M.A., S.S. Arcot, et al (1996). "Genetic variation of recent Alu insertions in human populations." J Mol Evol 42:22–29.

Shriver, M.D., M.W. Smith, et al (1997). Ethnic–affiliation estimation by use of population–specific DNA markers. Am. J. Hum. Genet. 60:957–964.

Deininger, P.L., A.R. Knight, et al (Oct. 29, 1996). A hypervariable region of the low denisty lipoprotein receptor gene for use in studies of human diversity. Presented and abstract published at the Annual Meeting of the American Society for Human Genetics.

Knight, A., M.A. Batzer, et al (1996). "DNA sequences of Alu elements indicate a recent replacement of the human autosomal genetic complement." Proc. Natl. Acad. Sci. USA 93:4360–4364.

* cited by examiner

*Primary Examiner*—Jeffrey Fredman
(74) *Attorney, Agent, or Firm*—Michael L. Murray

(57) ABSTRACT

The polymorphic character of a sequence of the human genome comprising approximately 950 base pairs and methods for using it to determine human identification and parentage are disclosed.

10 Claims, 1 Drawing Sheet

HIGH DENSITY POLYMORPHIC GENETIC LOCUS

OBJECTIVES AND SIGNIFICANCE

A need exists for characterized human nuclear loci that could be analyzed for diversity in a reasonably rapid way. Such diversity, or polymorphism, is useful for establishing human identity, often for forensic purposes. In addition, diversity is useful for establishing parentage. The use of polymorphism for these purposes and the methods to do so are described by the Committee on DNA Forensic Science, *The Evaluation of Forensic DNA Evidence*, National Academy Press, Washington, D.C., (1996) and by Walker, *Inclusion Probabilities in Parentage Testing*, American Association of Blood Banks, Arlington, Va. (1983). An in-depth analysis of genetic, ethnic and geographical variation is provided by Cavalli-Sforza et al. (*The History and Geography of Human Genes*. Princeton University Press, Princeton, N.J. (1994)). Nei (*Molecular Population Genetics*. Columbia University Press, New York (1987) provides a general discussion of the principles of population genetics.

Most human nuclear regions, however, show so little diversity that analysis requires sequencing of very long genomic regions to be informative. Regions of the genome that are hypervariable overcome this difficulty by allowing a significant amount of sequence variation in a shorter DNA sequence, providing a tremendous benefit for studies of human diversity and molecular anthropology.

Additional information can be derived from linkage disequlibrium of polymorphisms. Disequilibrium among polymorphisms can be correlated with ethnic origins and thus used to provide information about ethnic descent of an individual from his DNA.

Others have used length polymorphisms (e.g., VNTRS and microsatellites (Nakamura et al, 1987; Bowcock et al, 1994; Deka et al, 1995) or minisatellites (Amour et al, 1996), or combinations of markers for linkage disequilibirum studies (Tishkoff et al, 1996). These existing technologies are limited by low levels of polymorphism and complex analytical methods.

Analyses that utilize DNA sequence of point mutations directly avoid these problems, but only if the polymorphism density within the selected sequence is high. By analyzing a region with a high density of sequence variation, a large amount of useful information can be obtained from a short sequence.

BRIEF DESCRIPTION OF THE INVENTION

DEFINITIONS

All of the terms used in the specification and the claims are known to one skilled in the act. Nevertheless, in order to provide a clear and consistent understanding of the specification and the claims, including the scope given to such terms, the following definitions are provided.

Polymorphic locus or gene: A nucleic acid sequence localized in the diploid genome wherein the homologous copies are not identical.

Nucleotide diversity is the average number of nucleotide differences per site between any two randomly chosen sequences. This term and related concepts are further explained in Li and Grauer, *Fundamentals of Molecular Evolution*, Sinauer Associates, Inc., Pub., (1991).

The term "haplotype" means the set of alleles linked on a single chromosome.

The term "genotype" means the set of alleles present in an individual.

Alu sequences comprise a family of generally nonfunctional processed pseudogenes. Alu elements are DNA sequences that are approximately 300 bp long that belong to a family of repeated sequences. Alu family members appear more than 500,000 times in the human genome, constituting 5–6% of the genome (see Li and Grauer, *Fundamentals of Molecular Evolution*, Sinauer Associates, Inc., Pub., (1991).

The term "amplifying" which typically refers to an "exponential" increase in target nucleic acid is being used herein to describe both linear and exponential increases in the numbers of a select target sequence of nucleic acid.

The term "amplification" refers to any in vitro means for multiplying the copies of a target sequence of nucleic acid. Such methods include but are not limited to those discussed herein. Sequence-based amplification systems such as the polymerase chain reaction (PCR), nucleic acid sequence-based amplification (NASBA) (see Sooknanan and Malek, 1995, Biotechnology, 13: 563–564), and strand displacement amplification (SDA) (see Walker et al., 1994, Nucleic Acids Res.) amplify a target nucleic acid sequence. Signal-based amplification such as oligonucleotide ligation assay (OLA), Q.β. RNA replicase (Lizardi and Kramer. 1991. TIB 9: 53–58), cycling probe reaction (CPR) (Duck et al. 1991. Biotechniques 9: 142–147) and branched DNA (bDNA) (Urdea. 1993. Clin. Chem. 39: 725–726), amplify or alter a signal from a detection reaction that is target dependent.

The term "amplifying" which typically refers to an "exponential" increase in target nucleic acid is being used herein to describe both linear and exponential increases in the numbers of a select target sequence of nucleic acid.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is initiated, i.e., in the presence of four different nucleoside triphosphates and a DNA polymerase in an appropriate buffer ("buffer" includes pH, ionic strength, cofactors, etc.) and at a suitable temperature. Several methods of amplification that use primers have been devised, the best known being PCR. For example, in Stand Displacement Amplification (SDA), the 3' end of the amplification primer (the target binding sequence) hybridizes at the 3' end of the target sequence and comprises a recognition site for a restriction enzyme near its 5' end.

The term "thermocycling profile" as used herein refers to the selected temperature parameters selected for "n" cycles of amplification. The thermocycling profile includes at least two temperatures, a high denaturation temperature, adequate for sample-template, and subsequent product, denaturation, and a low temperature appropriate for primer annealing and polymerase extension. Accordingly, particular thermocycling parameters are selected to control primer annealing and product denaturation and thus regulate accessibility and primer extension.

The choice of primers for use in PCR determines the specificity of the amplification reaction. Primers used in the present invention are generally oligonucleotides, usually deoxyribonucleotides several nucleotides in length, that can be extended in a template-specific manner by the polymerase chain reaction. The primer is sufficiently long to prime the synthesis of extension products in the presence of the agent for polymerization and typically contains 10–30 nucleotides, although that exact number is not critical to the successful amplification.

A primer is selected to be "substantially" complementary to a strand of the template having a specific sequence. For primer extension to occur, the primer must be sufficiently complementary to anneal to the nucleic acid template under the reaction conditions. Not every nucleotide of the primer must anneal to the template for primer extension to occur. The primer sequence need not reflect the exact sequence of the template. For example, in one embodiment of the invention, a non-complementary nucleotide fragment or tail is attached to the 5' end of the primer with the remainder of the primer sequence being complementary to the template.

Alternatively, non-complementary bases can be interspersed into the primer, provided that the primer sequence has sufficient complementarity with the template for hybridization to occur and allow synthesis of complementary DNA strand.

As used herein in referring to primers, probes, or secondary oligonucleotides, the term "oligonucleotide" refers to a molecule comprised of two or more deoxyribonucleotides or ribonucleotides, and preferably more than three. Its exact size is not critical (except as noted herein), but the size depends upon many factors including the ultimate use or function of the oligonucleotide. The oligonucleotide may be derived synthetically, by cloning or by other methods known in the art.

In some situations where mismatches between the targeted nucleic acid and a primer are suspected, the effect of the mismatch may be overcome using specialized primer compositions, such as those described for example in EP-A-0 393 743 (published Oct. 24, 1990) and EP-A-0 417 842 (published Mar. 20, 1991).

Competitive oligonucleotide priming (COP), distinguishes closely related DNA sequences by comparing competitive annealing of two or more DNA sequences closely matched to the DNA sequence of interest. While the selected primer need not reflect the exact sequence of the template in the competitive oligonucleotide primer assay, it is important that the different sequences used as competitive oligonucleotide primers have different denaturation temperatures. For example, in the detection of a normal genetic sequence, the competitive oligonucleotide primers could include a primer which is an exact copy of the complementary strand to the normal genetic sequence and a primer which is a copy of the complementary strand with one base pair mismatched. Both a perfectly matched primer and a primer with a single DNA base mismatch are able to bind to the template. However, when the two closely related primers are incubated together with the DNA template, the binding of the perfectly matched primer will be favored over a primer with a single base mismatch. Alternatively, one of the primers can contain one base mismatch to the known genetic sequence and the other oligonucleotides would contain at least two mismatches. Thus, the requirements are that one of the sequences have N mismatches and the other sequence or sequences have greater than N mismatches, where N can be from zero to any number of mismatches which will still provide a substantially similar sequence able to bind. When two oligonucleotides differing by a single DNA base are supplied as primers in a reaction containing a single DNA or RNA template then the perfectly matched oligonucleotide primer will be highly favored over the primer with the single base mismatch. Similarly, if neither primer is a perfect match the more closely matched primer will be favored. The greater the difference between the sequence of interest and the other sequences, the more efficiently the competitive oligonucleotide primer assay functions. However, when the difference is too great, it may no longer function as a competitive assay.

Some detection technologies require perfect complimentary between oligonucleotides, whether used as probes or primers. In particular, allele discriminating nucleic acid sequence detection technologies are those which discriminate against sequences that vary by as little as one internally located nucleotide. Any mismatched sequences, even by a single nucleotide, are non-targets for these technologies.

By "homogeneous" is meant that the process does not require a separation of the detected target nucleic acid from nontargeted materials.

Fluorescence resonance energy transfer (FRET) is a well known spectroscopic phenomenon that has been exploited in oligonucleotide labeling schemes involving pairs of fluorescent dyes. In all of these schemes pairs of dyes are coupled in such a way that a signal is generated showing indicated whether the dyes are coupled by FRET or a FRET-like mechanism. The use of such pairs and FRET coupling is well known to those skilled in the art. Several homogeneous genotyping methods based on PCR amplification and FRET detection have recently been described. The design and synthesis of FRET dye-labeled oligonucleotides is described by Ju et al (1995, Anal. Biochem. 231: 131–140; and Benson, et al, 1995, 231: 247–255).

SUMMARY OF THE INVENTION

Figure 1:
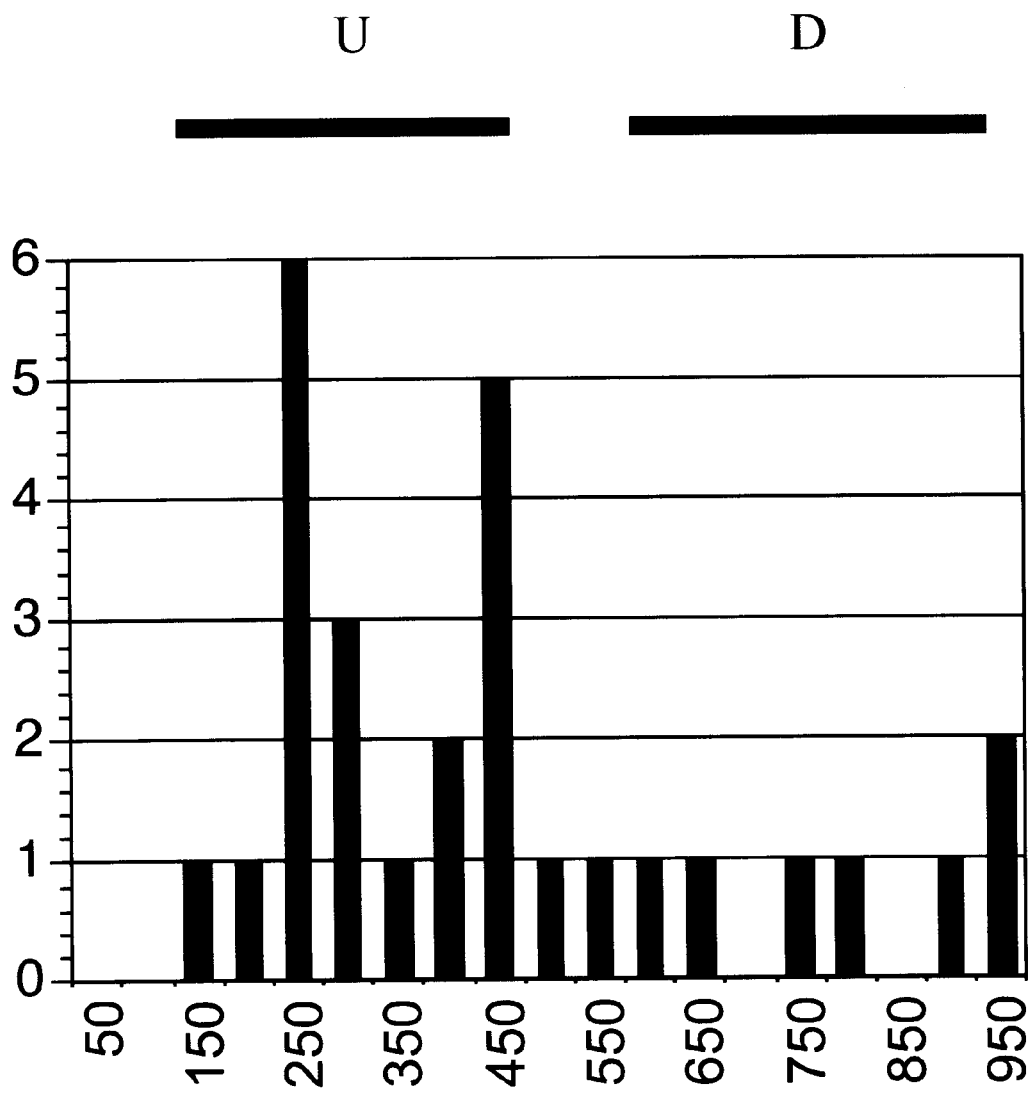
FIG. 1 Histograms depicting number of base substitutions per 50 bp segments of human (a) and other species (b) sequences shown in FIGS. 1 and 2. Two complete Alu elements, U and D, are located as indicated by bars. Alu U has been gene converted in humans, and has not undergone gene conversion in the other species (see text). Note that variation is highest in Alu U. in both the gene converted form in humans, and the non-gene converted form in other species. As with other Alu loci, increased variation is also present in the 5' polyadenine tail of the Alu elements. Given the recent common ancestry of all modern humans, and the multi-million year divergence dates among species, the rate is far higher in humans. In humans, variation in Alu U is two orders of magnitude higher than for other human non-coding nuclear loci. In other hominoid species, variation in Alu U is about three times that of most other nuclear loci, and the variation contains strong phylogenetic signal (see text).

Haplotypes are obtained from analysis of a specific 950 bp sequence from within the human low density lipoprotein receptor gene. Haplotypes from human donors of known ethnic origin are compared with an expected haplotype frequency. The expected frequency is estimated from the allele frequencies of the polymorphisms detected, assuming random distribution. A discriminant coefficient is estimated from the discrepancy between the frequency of the observed haplotypes of each ethnic group and the expected haplotype frequency. This coefficient is used as a predictor of ethnic descent.

In addition, the 950 bp region of the LDLR gene is used to identify individuals and parentage using methodology well known to those skilled in the art

DETAILED DESCRIPTION OF THE INVENTION

The nuclear genome evolves at a slow rate and therefore requires a large effort to characterize sufficient diversity to be informative about identity or descent. Thus, many studies utilize highly polymorphic markers, such as VNTRs and microsatellites (Nakamura et al, 1987; Bowcock et al, 1994; Deka et al, 1995) or minisatellites (Amour et al, 1996) to look at populations. An alternative is the distinctive markers resulting from insertions of transposable elements (Batzer et al, 1995), the use of RFLPs (Bowcock et al, 1991; Botstein et al, 1980), or combination of markers for linkage disequilibrium studies (Tishkoff et al, 1996). But because of the low number of alleles and the plus/minus nature of many of these types of markers, each marker provides little detailed information and for many it is difficult to determine whether identity of size is due to identity of descent. Analyses that utilize DNA sequence of point mutations directly avoid these problems by revealing the ultimate source of genetic variation and evolution.

A series of Alu insertion markers have been utilized to obtain information about identity and descent, and they are informative. Nevertheless, each dimorphic Alu allele supplies only a limited amount of information.

Sequencing can supply information about the linkage of multiple allelic changes or haplotypes that can be useful in assessing relationships. We have discovered a region of the low density lipoprotein receptor (LDLR) gene that has sufficient diversity and polymorphism density to make the use of single nucleotide polymorphisms (SNPs) a productive alternative.

LDLR and recombination.

The LDLR gene has a number of unusual properties which may be connected in some way to the high level of diversity we have detected. First, the LDLR gene is known to contain a high density of Alu repeats (Horsthemke et al, Eur. J Biochem, 164: 77–81 (1987). Second, the LDLR gene locus shows a high level of inter-Alu recombinations that lead to gene defects (Horsthemke et al, Lehrman et al, Cell 48: 827–835 (1987). Third, the LDLR gene region has been found to contain a number of recombination hot spots, based on studies of linkage disequilibrium in human populations (Miserez et al, Am. J. Hum Genet 52: 808: 826 (1993).

Lastly, there are subfamilies of Alu repeats that have specific diagnostic mutations depending on the time of the Alu insertion (Knight et al, Proc. Natl. Acad. Sci. 93: 4360–4364 (1996). One of the Alus in the diverse region is the only known case of an older Alu subfamily member that has converted to a younger subfamily sequence (Kass et al, Mol Cell Biol 15: 19–25, (1995). Thus, in general this locus seems to be subject to a number of recombination-related processes.

Other hypervariable regions.

Several regions of the nuclear genome with high nucleotide diversity are known. The MHC locus has been found to be highly variable with survival of a number of ancient alleles (Boyson, Immunogenetics 41, 59–68 (1995)). Survival of variability within the MHC locus is generally attributed to functional selection for diverse genetic variants at the MHC. Functional selection for variants counters the normal effect of genetic drift and results in the survival of genetic variants. The other regions that show diversity are the variable regions of immunoglobin genes. These regions are subject to a very high mutation rate (MacLennan, Curr. Biol. 4, 70–72 (1994)); thus creating greater diversity in immunoglobin molecules. In this case, the observed diversity is attributed to the high mutation rate, and not to functional selection for variants. Thus, there are precedents for the presence of high levels of genetic diversity due to high mutation rate, as well as an inability of fixation by genetic drift to eliminate ancestral allelic diversity.

Three different neutral nuclear human loci, comprising 55 kb total, that encompass Alu repeats have been sequenced for multiple representatives of diverse human population groups. Most individuals and populations showed absolutely no variation in these three loci, with one locus showing no allelic variation at all, a second showing only one minor allele and a third with two minor alleles. Each of the minor alleles represented only a single base change from the consensus. Thus, as is expected from a number of other studies (Bowcock, Proc. Natl. Acad. Sci. 88, 839–844 (1991); Li, Genetics 129, 513 (1991); Fullerton, Proc. Natl. Acad. Sci. 91, 1805 (1994)), human nuclear genetic diversity is extremely low. This low diversity makes it difficult to utilize the nuclear genome for many types of studies because the amount of sequencing that is necessary to obtain sufficient diversity for analysis is prohibitive.

One of the Alu family members in the 3'-untranslated region (UTR) of the LDL receptor mRNA unexpectedly contained 19 bp differences (Kass, Mol. Cell Biol. 15, 19–25 (1995)). In sequencing several isolates of this gene-converted Alu we have noted considerable heterogeneity. In fact, out of the 14 individuals that we have sequenced across this one Alu region, there are 12 different alleles (see Table 1 for a portion of these data). They diverge from the consensus at about 1% of the bases within the body of the Alu (excluding the normally variable A tail also). This represents about 50 times the diversity of other typical neutral human DNA sites.

The region of interest spans 950 aligned positions among representatives of diverse human populations. It is defined by PCR primers that anneal to orthologous sites. It is within the 3' untranslated region (UTR) of the low density lipoprotein receptor (LDLR) gene. This region includes unique sequence and two complete Alu elements, one spanning position 117 to 428 (Alu U, upstream) and the other spanning positions 595 to 911 (Alu D, downstream) in Table 1. A partial alu element is present from positions 462 to 591. In non-human primates, Alus U and D are members of the primate-specific (PS) alu subfamily that is present in all primates. In humans alu U has been gene converted by a younger, Sb2 subfamily member. The entire region has maintained a higher level of variation than other known nuclear regions. Comparisons of average divergence or nucleotide deiversity and a tally of the local number of base differences within the region among human populations (FIG. 1) show a high level of diversity.

Additional sequences for German Caucasions (GC) and African-Americans are provided in Table 2.

Among humans nucleotide diversity is 1.98±0.39% for Alu U and 0.54±0.19% for alu D. The 5' polyadenine tails of Alu U and D were not considered for these calculations. Table 3 contains a comparative list of the values of nucleotide diversity for an assortment of genetic loci.

TABLE 1

Portion of the 3' untranslated region of the low density lipoprotein receptor gene of eight individual humans representing diverse populations. Dots indicate identity with hypothetical common ancestral sequence (HUMCON). HUMCON is the most prevalent sequence to date. Dashes maintain alignment in regions of length variation. No two individuals are identical, in contrast to virtual monomorphism among diverse human populations at other nuclear loci. PUBLI = published sequence, AFRIC = African American, INDIA = Indian, INUIT = Greenland Inuit, NEWGU = New Guinean, PYGMY = African Pygmy, ESKIM = Alaskan Eskimo, INDON = Indonesian.

| | | | | | | | | | | | | | | | | | | |
|---|---|---|---|---|---|---|---|---|---|---|---|---|---|---|---|---|---|---|
| HUMCON | CATTGTCGTC | TTTATGTCCG | CCCACCTAGT | GCTTCCACTT | CTATGCAAAT | GCCTCCAAGC | CATTCACTTC | CCCAATCTTG | TCGTTGATGG | GTATGTGTTT |
| abor2 | .....T.... | .......... | .T........ | .......... | .......... | .......... | .......... | .....G.... | .......... | .....C.... |
| indo2 | .......... | .......... | .......... | .......... | .......... | .......... | .......... | .......... | .......... | .......... |
| pygmy | .......... | .......... | .......... | .......... | .......... | .......... | .......... | .......... | .......... | .......... |
| E3 | .......... | .......... | .......... | .......... | .......... | .......... | .......... | .......... | .......... | .......... |
| inuit | .......... | .......... | .......... | .......... | .......... | .......... | .......... | .......... | .......... | .......... |
| ngui8 | .......... | .......... | .......... | .......... | .......... | .......... | .......... | .......... | .......... | .......... |
| publi | .......... | .......... | .......... | .......... | .......... | .......... | .......... | .......... | .......... | .......... |
| Indl | .......... | .......... | .......... | .......... | .......... | .......... | .......... | .......... | .......... | .......... |
| AA2 | .......... | .......... | .......... | .......... | .......... | .......... | .......... | .......... | .......... | .......... |
| HUMCON | AAAACATGCA | CGGTGAGGCC | GGGCGCAGTG | GTCCTCACGCC | TGTAATCCCA | GCACTTTGGG | AGGCCGAGGC | GGGTGGATCA | -TGAGGTCA | GGAGATCGAG |
| abor2 | .......... | .......... | .......... | .......... | .......... | .......... | ....A..... | .....C.... | CC....... | ....T..... |
| indo2 | .......... | .......... | .......... | .......... | .......... | .......... | ....A..... | .......... | ---- | .......... |
| pygmy | .......... | .......... | .......... | .......... | .......... | .......... | ....A..... | .......... | ---- | .......... |
| E3 | .......... | .......... | .......... | .......... | .......... | .......... | .......... | .......... | ---- | .......... |
| inuit | .......... | .......... | .......... | .......... | .......... | .......... | .......... | .......... | ---- | .......... |
| ngui8 | .......... | .......... | .......... | .......... | .......... | .......... | .......... | .......... | ---- | .......... |
| publi | .......... | .......... | .......... | ..C....... | .......... | .......... | .......... | .......... | ---- | .......... |
| Indl | .......... | .......... | .......... | ..C....... | .......... | .......... | .......... | .......... | ---- | .......... |
| AA2 | .......... | .......... | .......... | ..C....... | .......... | .......... | .......... | .......... | ---- | .......... |
| HUMCON | ACCATCCTGG | CTAACAAGGT | GAAACCCCGT | CTCTACTAAA | AATACAAAAA | ATTAGCCGGG | CGCGGTGGCG | GCACCTGTA | GTCCCAGCTA | CTCGGGAGGC |
| abor2 | ...G...... | .C....T... | ....T.T... | .T........ | G......... | -......... | T.T......A | T.G...- | A......... | .......... |
| indo2 | .......... | .......... | .......... | .......... | .......... | .......... | .......... | .......... | .......... | .......... |
| pygmy | .......... | .......... | .......... | .......... | .......G.. | .......... | .......... | .......... | .......... | .......... |
| E3 | .......... | .......... | .......... | .......... | .......... | .......... | .......T.. | .......... | .......... | .......... |
| inuit | .......... | .......... | .......... | .......... | .......... | .......... | .......T.. | .......... | .......... | .......... |
| ngui8 | .......... | .......... | .......... | .......... | .......... | .......... | .......... | .......... | .......... | .......... |
| publi | .......... | .......... | .......... | .......... | .......... | .......... | .......T.. | .......... | .......... | .......... |
| Indl | .......... | .......... | .......... | .......... | .......... | .......... | .......... | .......... | .......... | .......... |
| AA2 | .......... | .......... | .......... | .......... | .......... | ....T..... | .......T.. | .....T.... | .......... | .......... |
| HUMCON | TGAGGCAGGA | GAATGGTGTG | AA--CCCGG | GAAGCGGAGC | TTGCAGTGAG | CCGAGATTGC | GCCACTGCAG | TCCCAGTCT | GGCCTGGGCG | ACA----G |
| abor2 | .......... | ...C.CT.A | .GGAA...A | ..G..A..G | .A......T | .T......T | .T.T..AGC | .AGCC--... | ------..T. | ATGACA. |
| indo2 | .......... | .......... | .......... | ..G..A..G | .......... | .......... | ......AGC | .......C | .......... | .--------- |
| pygmy | .......... | .......... | .......... | .........G | .......... | .......... | .......... | .......C | .......... | .--------- |
| E3 | .......... | .......... | .......... | .........G | .......... | .......... | .......... | .......C | .......... | .--------- |
| nuit | .......... | .......... | .......... | .........G | .......... | .......... | .......... | .......... | .......... | .--------- |
| ngui8 | .......... | .......... | .......... | .......... | .......... | .......... | .......... | .......... | .......... | .--------- |
| publi | .......... | .......... | .......... | .......... | .......... | .......... | .......... | .......... | .......... | .--------- |
| Indl | .......... | .......... | .......... | .......... | .......... | .......... | .......... | .......... | .......... | .--------- |
| AA2 | .......... | .......... | .......... | .......... | .......... | .......... | .......... | .......... | .......... | .--------- |

TABLE 1-continued

Portion of the 3' untranslated region of the low density liproprotein receptor gene of eight individual humans representing diverse populations. Dots indicate identity with hypothetical common ancestral sequence (HUMCON). HUMCON is the most prevalent sequence to date. Dashes maintain alignment in regions of length variation. No two individuals are identical, in contrast to virtual monomorphism among diverse human populations at other nuclear loci. PUBLI = published sequence, AFRIC = African American, INDIA = Indian, INUIT = Greenland Inuit, NEWGU = New Guinean, PYGMY = African Pygmy, ESKIM = Alaskan Eskimo, INDON = Indonesian.

| | | | | | | | | | | |
|---|---|---|---|---|---|---|---|---|---|---|
| HUMCON | AG-CGAGACT | CCGTCTCAAA | AAAAAAAAAA | AAAAAAAAAA | CCATGCATGG | TGCATCAGCA | GCCCANNGCC | TCTGGCCAGG | CATGGCCAGG | CTGAGGTGGG |
| abor2  | ..CT..A... | .......... | .......... | .......... | .......C.. | .......... | .......... | .......... | .......... | .......... |
| indo2  | .-.T...... | .......... | .......... | .......... | .......... | .......... | ...G..N... | .......... | .......... | .......... |
| pygmy  | .-........ | ---....... | .......... | .......... | .......... | .......... | -----G.... | .......... | .......... | .......... |
| E3     | .-........ | .......... | .......... | .......... | .......... | .......... | .......... | .......... | .......... | .......... |
| inuit  | .-........ | .......... | .......... | ........C. | .......... | .......... | .....N.... | .......... | .......... | .......... |
| ngui8  | .-........ | .......... | .......... | ........C. | .......... | .......... | ......TG.. | .......... | .......... | .......... |
| publi  | .-........ | .......... | .......... | ........C. | .......... | .......... | .......... | .......... | .......... | .......... |
| Indl   | .-........ | .......... | .......... | -......... | .......... | .......... | ......TG.. | .......... | .......... | .......... |
| AA2    | .......... | .......... | .......... | ........C. | .......... | .......... | .......... | .......... | .......... | .......... |
| HUMCON | AGGATGGTTT | GAGCTCAGGC | ATTTGAGGCT | GTCGTGAGCT | ATGATTATGC | CACTGCTTTC | CAGCCTGGGC | AACATAGTAA | GACCCCATCT | CTTAAAAAAT |
| abor2  | .......... | .......... | .......... | .......... | .......... | .......... | .......... | .......... | .......... | .......... |
| indo   | .......... | .......... | .......C.. | .......... | .......... | .......... | .......... | .......... | .......... | .......... |
| pygmy  | .......... | .......... | .......C.. | .......... | .......... | .......... | .......... | .......... | .......... | .......... |
| E3     | .......... | .......... | .......C.. | .......... | .......... | .......... | .......... | .......... | .......... | .......... |
| inuit  | .......... | .......A.. | .......... | .......... | .......... | .......... | .......... | .......... | .......... | .......... |
| ngui8  | .......... | .......... | .......... | .......... | .......... | .......... | .......... | .......... | .......... | .......... |
| publi  | .......... | .......... | .......... | .......... | .......... | .......... | .......... | .......... | .......... | .......... |
| Indl   | .......... | .......... | .......... | .......... | .......... | .......... | .......... | .......... | .......... | .......... |
| AA2    | .......... | .......... | .......... | .......... | .......... | .......... | .......... | .......... | .......... | .......... |
| HUMCOM | GAATTTGGCC | AGACACAGGT | GGCTCACGCC | TGTAATCCCA | GCACTTTGGG | AGGCTGAGCT | GGATCACTTG | AGTTCAGGAG | TTGGAGACCA | GGCCTGAGCA |
| abor2  | .......... | .......... | .......... | .......... | .......... | .......... | .......... | .......... | .......... | .......... |
| indo2  | .......... | .T........ | .......... | .......... | .......... | .......... | .......... | .......... | .......... | .......... |
| pygmy  | .......... | .T........ | .......... | .......... | .......... | .......... | .......... | .......... | .......... | .......... |
| E3     | .......... | .T.G...... | .......... | .......... | .......... | .......... | .......... | .......... | .......... | .......... |
| inuit  | .......... | .......... | .......... | .......... | .......... | .......... | .......... | .......... | .......... | .......... |
| ngui8  | .......... | .......... | .......... | .......... | .......... | .......... | .......... | .......... | .......... | .......... |
| publi  | .......... | .......... | .......... | .......... | .......... | .......... | .......... | .......... | .......... | .......... |
| Indl   | .......... | .......... | .......... | .......... | .......... | .......... | .......... | .......... | .......... | .......... |
| AA2    | .......... | .......... | .......... | .......... | .......... | .......... | .......... | .......... | .......... | .......... |
| HUMCOM | ACAAAGCGAG | ATCCCATCTC | TACAAAAACC | AAAAAGTTAA | AAATCAGCTG | GGTACGGTGG | CACGTGCCTG | TGATCCCAGC | TACTTGGGAG | GCTGAGGCAG |
| abor2  | .......... | .......... | .......... | .......... | .......... | .......... | .......... | .......... | .......... | .......... |
| indo2  | .......... | .......... | .......T.. | .......... | .......... | .T........ | .......... | .......... | .......... | .......... |
| pygmy  | .......... | .......... | .......... | .......... | .......... | .......... | .......... | .......... | .......... | .......... |
| E3     | .......... | .......... | .......... | .......... | .......... | .......... | .......... | .......... | .......... | .......... |
| inuit  | .......... | .......... | .......... | .......... | .......... | ....T..... | .......... | .......... | .......... | .......... |
| ngui8  | .......... | .......... | .......... | .......... | .......... | .......... | .......... | .......... | .......... | .......... |
| publi  | .......... | .......... | .......... | .......... | .......... | ....T..... | .......... | .......... | .......... | .......... |
| Indl   | .......... | .......... | .......... | .......... | .......... | ....T..... | .......... | .......... | .......... | .......... |
| AA2    | .......... | .......... | .......... | .......... | .......... | .......... | .......... | .......... | .......... | .......... |
| HUMCON | GAGGATCGCC | TGAGCCCAGG | AGGTGGAGGT | TGCAGTGAGC | CATGGATCGAG | CCACTGCACT | CCAGCCTGGG | CAACAGATGA | AGACCCTATT | TCAGAAATAC |
| | | | | | | | | | ...C...... | |

TABLE 1-continued

Portion of the 3' untranslated region of the low density liproprotein receptor gene of eight individual humans representing diverse populations. Dots indicate identity with hypothetical common ancestral sequence (HUMCON). HUMCON is the most prevalent sequence to date. Dashes maintain alignment in regions of length variation. No two individuals are identical, in contrast to virtual monomorphism among diverse human populations at other nuclear loci. PUBLI = published sequence, AFRIC = African American, INDIA = Indian, INUIT = Greenland Inuit, NEWGU = New Guinean, PYGMY = African Pygmy, ESKIM = Alaskan Eskimo, INDON = Indonesian.

| | | | | | | |
|---|---|---|---|---|---|---|
| abor2 | ........... | ........... | ........... | ........... | ........... | ........... |
| indo2 | ........... | ........... | ........... | ........... | ........... | ........... |
| pygmy | ........... | ........... | ........... | ........... | ........... | ........... |
| E3 | ........... | ........... | ........... | ........... | ........... | ........... |
| publi | ........... | ........... | ........... | ........... | ........... | ........... |
| inuit | ........... | ........... | ........... | ........... | ........... | ........... |
| ngui8 | ........... | ........... | ........... | ........... | ........... | ........... |
| Ind1 | ........... | ........... | ........... | ........... | ........... | ........... |
| AA2 | ........... | ........... | ........... | ........... | ........... | ........... |
| HUMCON | ACCTATAAAA | AAA-TAAATA | AATCCTCCAG | TCTGGATCGT | TTGACGGGAC | TTCAGTTTCT |
| abor2 | ........... | ...AA.---- | ...T...... | ........... | ........... | TT |
| indo2 | ........... | ...-...... | ........... | ........... | ........... | .. |
| pygmy | ........... | ...-...... | ........... | ........... | ........... | .. |
| E3 | ........... | ...A...... | ........... | ........... | ........... | .. |
| publi | ........... | ........... | ........... | ........... | ........... | ........... |
| Inuit | ........... | ...-...... | ........... | ........... | ........... | ........... |
| ngui8 | ........... | ........... | ........... | ........... | ........... | ........... |
| Ind1 | ........... | G..-...... | .-........ | ........... | ........... | ........... |
| AA2 | ........... | ........... | ........... | ........... | ........... | ........... |

TABLE 2

Same genomic region, depicted in the same manner as FIG.1
for German-Caucasians and African-Americans.

```
GC-8/1.GW    CATTGTCGTC TTTATGTCCG CCCACCTAGT GCTTCCACTT CTATGCAAAT    50
GC-7/1.GW    CATTGTCGTC TTTATGTCCG CCCACCTAGT GCTTCCACTT CTATGCAAAT    50
GC-4/1.GW    CATTGTCGTC TTTATGTCCG CCCACCTAGT GCTTCCACTT CTATGCAAAT    50
GC-3/1.GW    CATTGTCGTC TTTATGTCCG CCCACCTAGT GCTTCCACTT CTATGCAAAT    50
PUBL.GW      CATTGTCGTC TTTATGTCCG CCCACCTAGT GCTTCCACTT CTATGCAAAT    50

GC-8/1.GW    GCCTCCAAGC CATTCACTTC CCCAATCTTG TCGTTGATGG GTATGTGTTT   100
GC-7/1.GW    GCCTCCAAGC CATTCACTTC CCCAATCTTG TCGTTGATGG GTATGTGTTT   100
GC-4/1.GW    GCCTCCAAGC CATTCACTTC CCCAATCTTG TCGTTGATGG GTATGTGTTT   100
GC-3/1.GW    GCCTCCAAGC CATTCACTTC CCCAATCTTG TCGTTGATGG GTATGTGTTT   100
PUBL.GW      GCCTCCAAGC CATTCACTTC CCCAATCTTG TCGTTGATGG GTATGTGTTT   100

GC-8/1.GW    AAAACATGCA CGGTGAGGCC GGGCGCAGTG GC-TCACGCC TGTAATCCCA   149
GC-7/1.GW    AAAACATGCA CGGTGAGGCC GGGCGCAGTG G-CTCACGCC TGTAATCCCA   149
GC-4/1.GW    AAAACATGCA CGGTGAGGCC GGGCGCAGTG G-CTCACGCC TGTAATCCCA   149
GC-3/1.GW    AAAACATGCA CGGTGAGGCC GGGCGCAGTG G-CTCACGCC TGTAATCCCA   149
PUBL.GW      AAAACATGCA CGGTGAGGCC GGGCGCAGTG GCCTCACGCC TGTAATCCCA   150

GC-8/1.GW    GCACTTTGGG AGGCCGAGGC GGGTGGATCA TGAGGTCAGG AGATCGAGAC   199
GC-7/1.GW    GCACTTTGGG AGGCCGAGGC GGGTGGATCA TGAGGTCAGG AGATCGAGAC   199
GC-4/1.GW    GCACTTTGGG AGGCCGAGGC GGGTGGATCA TGAGGTCAGG AGATCGAGAC   199
GC-3/1.GW    GCACTTTGGG AGGCCGAGGC GGGTGGATCA TGAGGTCAGG AGATCGAGAC   199
PUBL.GW      GCACTTTGGG AGGCCGAGGC GGGTGGATCA TGAGGTCAGG AGATCGAGAC   200

GC-8/1.GW    CATCCTGGCT AACAAGGTGA AACCCCGTCT CTACTAAAAA TACAAAAAAT   249
GC-7/1.GW    CATCCTGGCT AACA-CGTGA AACCCCGTCT CTACTAAAAA TACAAAAAAT   248
GC-4/1.GW    CATCCTGGCT AACAAGGTGA AACCCCGTCT CTACTAAAAA TACAAAAAAT   249
GC-3/1.GW    CATCCTGGCT AACAAGGTGA AACCCCGTCT CTACTAAAAA TACAAAAAAT   249
PUBL.GW      CATCCTGGCT AACAAGGTGA AACCCCGTCT CTACTAAAAA TACAAAAAAT   250

GC-8/1.GW    TAGCCGGGCG CGGTGGTGGG CACCTGTAGT CCCAGCTACT CGGGAGGCTG   299
GC-7/1.GW    TAGCCGGGCG CGGTGGTGGG CACCTGTAGT CCCAGCTACT CGGGAGGCTG   298
GC-4/1.GW    TAGCCGGGCG CGGTGGTGGG CACCTGTAGT CCCAGCTACT CGGGAGGCTG   299
GC-3/1.GW    TAGCCGGGCG CGGTGGTGGG CACCTGTAGT CCCAGCTACT CGGGAGGCTG   299
PUBL.GW      TAGCCGGGCG CGGTGGTGGG CACCTGTAGT CCCAGCTACT CGGGAGGCTG   300

GC-8/1.GW    AGGCAGGAGA ATGGTGTGAA CCCGGGAAGC GGANNTTGCA GTGAGCCGAG   349
GC-7/1.GW    AGGCAGGAGA ATGGTGTGAA CCCGGGAAGC GGAGCTTGCA GTGAGCCGAG   348
GC-4/1.GW    AGGCAGGAGA ATGGTGTGAA CCCGGGAAGC GGANNTTGCA GTGAGCCGAG   349
GC-3/1.GW    AGGCAGGAGA ATGGTGTGAA CCCGGGAAGC GGANNTTGCA GTGAGCCGAG   349
PUBL.GW      AGGCAGGAGA ATGGTGTGAA CCCGGGAAGC GGAGCTTGCA GTGAGCCGAG   350

GC-8/1.GW    ATTGCGCCAC TGCAGTCCGC AGTCTGGCCT GGGCGACAGA GCGAGACTCC   399
GC-7/1.GW    ATCGCGCCAC TGCAGTCCGC AGTCTGGCCT GGGCGACAGA GCGAGACTCC   398
GC-4/1.GW    ATTGCGCCAC TGCAGTCCGC AGTCTGGCCT GGGCGACAGA GCGAGACTCC   399
GC-3/1.GW    ATTGCGCCAC TGCAGTCCGC AGTCTGGCCT GGGCGACAGA GCGAGACTCC   399
PUBL.GW      ATTGCGCCAC TGCAGTCCGC AGTCTGGCCT GGGCGACAGA GCGAGACTCC   400

GC-8/1.GW    GTCTC-AAAA AAAAAAAACA AAAAAAAACC ATGCATGGTG CATCAGCAGC   448
GC-7/1.GW    GTCTCAAAAA AAAAAAAACA AAAAAAAACC ATGCATGGTG CATCAGCAGC   448
GC-4/1.GW    GTCTCAAAAA AAAAAAAACA AAAAAAAACC ATGCATGGTG CATCAGCAGC   449
GC-3/1.GW    GTCTCAAAAA AAAAAAAACA AAAAAAAACC ATGCATGGTG CATCAGCAGC   449
PUBL.GW      GTCTCAAAAA AAACAAAACA AAAAAAAACC ATGCATGGTG CATCAGCAGC   450
```

TABLE 2-continued

Same genomic region, depicted in the same manner as FIG.1 for German-Caucasians and African-Americans.

| | | | | | | |
|---|---|---|---|---|---|---|
| GC-8/1.GW | CCATGGCCTC | TGGCCAGGCA | TGGCGAGGCT | GAGGTGGGAG | GATGGTTTGA | 498 |
| GC-7/1.GW | CCATGGCCTC | TGGCCAGGCA | TGGCGAGGCT | GAGGTGGGAG | GATGGTTTGA | 498 |
| GC-4/1.GW | CCATGGCCTC | TGGCCAGGCA | TGGCGAGGCT | GAGGTGGGAG | GATGGTTTGA | 499 |
| GC-3/1.GW | CCATGGCCTC | TGGCCAGGCA | TGGCGAGGCT | GAGGTGGGAG | GATGGTTTGA | 499 |
| PUBL.GW   | CCATGGCCTC | TGGCCAGGCA | TGGCGAGGCT | GAGGTGGGAG | GATGGTTTGA | 500 |

| | | | | | | |
|---|---|---|---|---|---|---|
| GC-8/1.GW | GCTCAGGCAT | TTGAGGCTGT | CGTGAGCTAT | GATTATGCCA | CTGCTTTCCA | 548 |
| GC-7/1.GW | GCTCAGGCAT | TTGAGGCTGT | CGTGAGCTAT | GATTATGCCA | CTGCTTTCCA | 548 |
| GC-4/1.GW | GCTCAGGCAT | TTGAGGCTGT | CGTGAGCTAT | GATTATGCCA | CTGCTTTCCA | 549 |
| GC-3/1.GW | GCTCAGGCAT | TTGAGGCTGT | CGTGAGCTAT | GATTATGCCA | CTGCTTTCCA | 549 |
| PUBL.GW   | GCTCAGGCAT | TTGAGGCTGT | CGTGAGCTAT | GATTATGCCA | CTGCTTTCCA | 550 |

| | | | | | | |
|---|---|---|---|---|---|---|
| GC-8/1.GW | GCCTGGGCAA | CATAGTAAGA | CCCCATCTCT | TAAAAAATGA | ATTTGGCCAG | 598 |
| GC-7/1.GW | GCCTGGGCAA | CATAGTAAGA | CCCCATCTCT | TAAAAAATGA | ATTTGGCCAG | 598 |
| GC-4/1.GW | GCCTGGGCAA | CATAGTAAGA | CCCCATCTCT | TAAAAAATGA | ATTTGGCCAG | 599 |
| GC-3/1.GW | GCCTGGGCAA | CATAGTAAGA | CCCCATCTCT | TAAAAAATGA | ATTTGGCCAG | 599 |
| PUBL.GW   | GCCTGGGCAA | CATAGTAAGA | CCCCATCTCT | TAAAAAATGA | ATTTGGCCAG | 600 |

| | | | | | | |
|---|---|---|---|---|---|---|
| GC-8/1.GW | ACACAGGTGC | CTCACGCCTG | TAATCCCAGC | ACTTTGGGAG | GCTGAGCTGG | 648 |
| GC-7/1.GW | ACACAGGTGC | CTCACGCCTG | TAATCCCAGC | ACTTTGGGAG | GCTGAGCTGG | 648 |
| GC-4/1.GW | ACACAGGTGC | CTCACGCCTG | TAATCCCAGC | ACTTTGGGAG | GCTGAGCTGG | 649 |
| GC-3/1.GW | ACACAGGTGC | CTCACGCCTG | TAATCCCAGC | ACTTTGGGAG | GCTGAGCTGG | 649 |
| PUBL.GW   | ACACAGGTGC | CTCACGCCTG | TAATCCCAGC | ACTTTGGGAG | GCTGAGCTGG | 650 |

| | | | | | | |
|---|---|---|---|---|---|---|
| GC-8/1.GW | ATCACTTGAG | TTCAGGAGTT | GGAGACCAGG | CCTGAGCAAC | AAAGCGAGAT | 698 |
| GC-7/1.GW | ATCACTTGAG | TTCAGGAGTT | GGAGACCAGG | CCTGAGCAAC | AAAGCGAGAT | 698 |
| GC-4/1.GW | ATCACTTGAG | TTCAGGAGTT | GGAGACCAGG | CCTGAGCAAC | AAAGCGAGAT | 699 |
| GC-3/1.GW | ATCACTTGAG | TTCAGGAGTT | GGAGACCAGG | CCTGAGCAAC | AAAGCGAGAT | 699 |
| PUBL.GW   | ATCACTTGAG | TTCAGGAGTT | GGAGACCAGG | CCTGAGCAAC | AAAGCGAGAT | 700 |

| | | | | | | |
|---|---|---|---|---|---|---|
| GC-8/1.GW | CCCATCTCTA | CAAAAACCAA | AAAGTTAAAA | ATCAGCTGGG | TATGGTGGCA | 748 |
| GC-7/1.GW | CCCATCTCTA | CAAAAACCAA | AAAGTTAAAA | ATCAGCTGGG | TACGGTGGCA | 748 |
| GC-4/1.GW | CCCATCTCTA | CAAAAACCAA | AAAGTTAAAA | ATCAGCTGGG | TATGGTGGCA | 749 |
| GC-3/1.GW | CCCATCTCTA | CAAAAACCAA | AAAGTTAAAA | ATCAGCTGGG | TATGGTGGCA | 749 |
| PUBL.GW   | CCCATCTCTA | CAAAAACCAA | AAAGTTAAAA | ATCAGCTGGG | TATGGTGGCA | 750 |

| | | | | | | |
|---|---|---|---|---|---|---|
| GC-8/1.GW | CGTGCCTGTG | ATCCCAGCTA | CTTGGGAGGC | TGAGGCAGGA | GGATCGCCTG | 798 |
| GC-7/1.GW | CGTGCCTGTG | ATCCCAGCTA | CTTGGGAGGC | TGAGGCAGGA | GGATCGCCTG | 798 |
| GC-4/1.GW | CGTGCCTGTG | ATCCCAGCTA | CTTGGGAGGC | TGAGGCAGGA | GGATCGCCTG | 799 |
| GC-3/1.GW | CGTGCCTGTG | ATCCCAGCTA | CTTGGGAGGC | TGAGGCAGGA | GGATCGCCTG | 799 |
| PUBL.GW   | CGTGCCTGTG | ATCCCAGCTA | CTTGGGAGGC | TGAGGCAGGA | GGATCGCCTG | 800 |

| | | | | | | |
|---|---|---|---|---|---|---|
| GC-8/1.GW | AGCCCAGGAG | GTGGAGGTTG | CAGTGAGCCA | TGATCGAGCC | ACTGCACTCC | 848 |
| GC-7/1.GW | AGCCCAGGAG | GTGGAGGTTG | CAGTGAGCCA | TGATCGAGCC | ACTGCACTCC | 848 |
| GC-4/1.GW | AGCCCAGGAG | GTGGAGGTTG | CAGTGAGCCA | TGATCGAGCC | ACTGCACTCC | 849 |
| GC-3/1.GW | AGCCCAGGAG | GTGGAGGTTG | CAGTGAGCCA | TGATCGAGCC | ACTGCACTCC | 849 |
| PUBL.GW   | AGCCCAGGAG | GTGGAGGTTG | CAGTGAGCCA | TGATCGAGCC | ACTGCACTCC | 850 |

| | | | | | | |
|---|---|---|---|---|---|---|
| GC-8/1.GW | AGCCTGGGCA | ACAGATGAAG | ACCCTATTTC | AGAAATACAA | CTATAAAAAA | 898 |
| GC-7/1.GW | AGCCTGGGCA | ACAGATGAAG | ACCCTATTTC | AGAAATACAA | CTATAAAAAA | 898 |
| GC-4/1.GW | AGCCTGGGCA | ACAGATGAAG | ACCCTATTTC | AGAAATACAA | CTATAAAAAA | 899 |
| GC-3/1.GW | AGCCTGGGCA | ACAGATGAAG | ACCCTATTTC | AGAAATACAA | CTATAAAAAA | 899 |
| PUBL.GW   | AGCCTGGGCA | ACAGATGAAG | ACCCTATTTC | AGAAATACAA | CTATAAAAAA | 900 |

TABLE 2-continued

Same genomic region, depicted in the same manner as FIG.1
for German-Caucasians and African-Americans.

```
GC-8/1.GW    A TAAATAAA TCCTCCAGTC TGGATCGTTT GACGGGACTT CAGGTTCTTT    947
GC-7/1.GW    A TAAATAAA TCCTCCAGTC TGGATCGTTT GACGGGACTT CAGGTTCTTT    947
GC-4/1.GW    A TAAATAAA TCCTCCAGTC TGGATCGTTT GACGGGACTT CAGGTTCTTT    948
GC-3/1.GW    A TAAATAAA TCCTCCAGTC TGGATCGTTT GACGGGACTT CAGGTTCTTT    948
PUBL.GW      AA TAAATAAA TCCTCCAGTC TGGATCGTTT GACGGGACTT CAGGTTCTTT    950
```

TABLE 3

| GENETIC LOCUS OR GENOME | NUCLEOTIDE DIVERSITY (%) | REFERENCE |
|---|---|---|
| Alu U | 1.98 | |
| Alu D | 0.54 | |
| mitochondrial genome | 0.3–0.4 | Merriwether, J. Mol. Evol. 33, 543–555 (1991). Cann, Nature 325, 31–36 (1987). |
| Alu in the a-globin gene | 0.027 | Knight, Proc. Natn. Acad. Sci. U.S.A. 80, 2290–2294 (1983). |
| 2.6 kb Alu-containing locus on Y chromosome | 0.037 | Hammer, Nature 378, 376–378 (1995). |
| 18.3 kb largely non-coding region of Y chromosome | 0.009 | Whitfield, Nature 378, 379–380 (1995). |
| Y chromosome zing-finger locus | monomorphic | Dorit, Science 268, 1183–1185 (1995). |

The comparative data of Table 3 have significant implications for the rate of evolution of Alus U and D. They strongly suggest a recent origin, since the diversity has occurred since the appearance of early modern humans in the fossil record at about 100,000 years ago. This indicates a rate of evolution of approximately 100 times that of other human nuclear loci. For the entire region, no two human sequences were identical, in contrast to virtual monomorphism at other nuclear loci. This level of diversity and rate of evolution make this highly polymorphic region useful for forensic analysis. The rapid evolution of this locus means that the allelic SNPs have not had time to approach equilibrium. Thus, haplotypes are associated with ethnic origins. For example, the haplotype of the aboriginal human shown in Table 1 is distinctively associated with that person's ethnic origin. Similarly, other distinctive haplotypes are apparent and more will become apparent as more individuals are examined.

The region of diversity in the five alleles with the gene-converted form of the Alu spans most of the Alu and into the flanking sequence (Table 1). However, it does not extend upstream of the Alu and shows only about half the divergence in the Alu B region. This is especially true as the change in the 900 region of Table 1 represents a change in the 3' A-rich region of the second Alu repeat, a type of region that is known for its high level of mutation (Economou et al, 1990; Arcot et al, 1995). Thus, there is a hot-spot for diversity, with the flanking sequences showing relatively low allelic diversity much like most other neutral nuclear loci, such as introns or pseudogenes. Further analysis of nucleotide substitutions in humans (Table 1) shows that all of the diversity does not represent random mutations, but instead represents a mixture of individual base changes associated with only one individual and a series of shared allelic changes through subgroups of the sequences. Most of these shared alleles (haplotypes) are also shared between individuals from diverse population groups, suggesting that they are relatively old alleles that spread through the populations with early human migrations.

Estimating Ethnic Affiliation

Polymorphic DNA sites are very powerful for distinguishing among individuals; nevertheless, most do not provide any suggestion concerning ethnic background or the physical characteristics of an individual. The pattern of haplotypes evident in the data for the genetic region of utilized by the present invention provides a basis for an embodiment of the invention. That embodiment is to utilize the diversity found in the 950 base pair described herein to obtain evidence concerning the ethnic background of an individual.

Shriver et al (Am. J. Hum. Genet., 60: 957–964 (1997)) provide a quantitative method to estimate ethnic affiliation from haplotypes. They have described a panel of separate population-specific alleles (PSAs) that enable robust ethnic-affiliation estimation (EAE). These alleles, however, lack the convenience and cost effectiveness of the single locus provided by the present invention.

Shriver et al provide a formula for calculating an average single-locus EAE log-likelihood ratio. The combined value of the EAE log-likelihood ratio for multiple loci can be calculated simply as the sum of the average single-locus log-likelihood ratios.

Dibennardo and Taylor (Am. J. Phys Anthropol 61: 305–314 (1983) and Iscan (Am. J. Phys Anthropol 62: 205–208 (1983)) used measurements of lengths and angles of bones to estimate a discriminant coefficient predictive of ethnic-affiliation.

Connor and Stoneking estimated ethnicity from human mitochondrial DNA types determined by hybridization with sequence-specific oligonucleotides. They used a logistic regression model to predict ethnic group.

EXPERIMENTAL DESCRIPTION

EXAMPLE 1

Cloning Then Sequencing

Cloning of the 950 base pairs of reported in Table 1 was performed using standard methods well known to those skilled in the art.

Amplification was performed using a set of six primers that allow unambiguous sequencing of the entire 950 bp on both strands. PCR amplification methodology well known to those skilled in the art was used.

EXAMPLE 2

Mixture of Direct Sequencing and Cloning

DNA Amplification

Total cellular DNAs were on hand in our laboratory stocks. These had been purified by conventional methods for previous studies. These DNA samples were used as template for PCR amplifications using reagents supplied by Perkin-Elmer including Amplitaq cloned DNA polymerase. PCR reactions were carried out in a Perkin-Elmer GeneAmp PCR System 9600 thermal cycler. Thermal cycle parameters were: denaturation at 94° for 15 seconds, annealing at 58° for 15 seconds, and extention at 72° for 20 seconds for 35 cycles with maximum ramp times. Cyclic amplification was initiated with a hot start at 94° for one minute and followed by a 2 minute terminal extension at 72°. Forward and reverse PCR primers were "F1039" (5'-ACTTCAAAGCCGTGATCGTGA-3') and "R2008" (5'-TGCAACAGTAACACGGCGATT-3').
Primer numbers indicate 3'-terminus position in published sequence of LDLR 3' UTR[33]. PCR products were sequenced directly or cloned using the TA system supplied by Stratagene.

Sequencing

Direct linear amplification thermal cycle sequencing[34,35] of double stranded PCR products was accomplished using exo⁻Pfu DNA polymerase and reagents supplied by Stratagene. Primers were end-labeled with $\gamma$-$^{32}$P ATP using T-4 polynucleotide kinase at 37° for 11 minutes followed by heat inactivation at 55° for 5 minutes. Sequencing reactions were carried out in a Hybaid OmniGene thermal cycler. Thermal cycle parameters were: denaturation at 95° for 30 seconds, annealing at 60° for 30 seconds, and extension at 72° for one minute. Cyclic sequencing was initiated with a hot start at 95° for one minute. The target region of the LDLR gene was sequenced using the external PCR primers, and internal primers

"F1209" (5'-CTCACGCCTGTAATCCCAGCACT-3'),

"F1501" (5'-ACCATGCATGGTGCATCAGCA-3').
Sequencing reactions were separated in 6% polyacrylamide, 8 M urea gels and visualized by autoradiography following overnight exposure.

The sequences obtained from example 2 are shown in Table 2.

PROSPECTIVE EXAMPLES

Prospective examples of other technologies applicable to analysis of the relevant genetic locus are described below.

In addition to the primers used in the examples, many primers flanking, or even within the relevant sequence are suitable for use for its amplification. In the case of the use of primers within the sequence, some sacrifice of terminal sequences would be made. Cloning also could be accomplished by a number of means well known to those skilled in the art.

Procedures for detecting point mutations fall into two main categories: (1) procedures which detect point mutations when the precise DNA sequence change can be anticipated; (2) procedures which "scan" for point mutations where the precise nature of the individual DNA gene change is not known. The present invention will work in either situation. The existence of heterozygous alleles gives rise to additional significant distinctions: (3) procedures which are useful in directly detecting polymorphisms in heterozygotic mixtures; (4) procedures which selectively amplify alleles, thus obviating the problem of heterozygotic mixtures. A recent review of genetic screening and scanning technologies is provided by Eng and Vijg (Nature Biotechnology 15: 422–426).

1. Procedures that are useful when the sequence can be anticipated.

A recently developed method that exemplifies a procedure that can detect SNPs when the sequence difference can be anticipated is that of Chen et al. (1997, Proc. Nat. Acad. Sci. USA., 94, 10756–10761 (1997)). Chen et al. recently described a DNA diagnostic assay that is said to be highly sensitive, specific, and cost-effective for detecting single base pair changes. The assay is a one-tube homogeneous assay that relies on fluorescence energy transfer between pairs of fluorescent dyes. The primer used requires only substantial homology. Using this assay, the identity of a base at any selected location can be determined by monitoring which FRET-coupled dye-labeled ddNTP is incorporated at that site. Changes in fluorescence intensities can be monitored in real time.

2. Examples of detection systems that are useful for unanticipated polymorphisms include the following.

Direct sequencing is the most accurate and most costly method to determine single nucleotide polymorphisms. Nevertheless, the presence of heterozygous SNPs can be problematic. For this reason new cost-effective methods of determining single nucleotide polymorphisms have been developed. Sequencing generally requires cloning DNA fragments before the sequencing reactions can be performed.

As an alternative, a variety of scanning techniques are used for single nucleotide polymorphism (SNP) detection. Cotton (TIG, 13: 43–46; Mutation Detection, Oxford University Press (1996), and Mutation Research, 285: 125–144 (1993) has reviewed scanning techniques. These include single-strand conformational polymorphism (SSCP), heteroduplex analysis, denaturing gradient gel electrophoresis (DGGE). SSCP, DGGE and heteroduplex methods can now detect almost 100% of SNPs. SSCP has recently been adopted to a high throughput technology that allows about 1000 PCR reactions to be analyzed in five tanks in 24 man hours. A radical modification is SSCP uses a commercially available enzyme "CLEAVASE I" to differentially digest the SSCP molecules, thus producing distinguishing patterns on agarose gels (Brow et al. Clin. Microbiol. These methods have low resolving power; i.e., they are not capable of precisely matching the SNP within the analyzed stretch of DNA. Other methods, including enzyme mismatch cleavage (EMC), chemical cleavage of mismatch (CCM), cleavase fragment length polymorphism, and RNase cleavage assay are more precise but still not exact. All of the methods require use of either special gels or gel electrophoresis conditions, or prolonged optimization of a reaction step.

A method for detecting genetic polymorphisms is described in Myers et al., 1989, PCR Technology, Ed. Erlich, Stockton Press, New York. According to the method, PCR primers are modified to affect the denaturation profile of the amplified DNA when the product is electrophoresed through a denaturation gradient gel after amplification. The modified primers include G-C polynucleotide tails which are referred to as G-C clamps because of the effect of increased G-C content on the thermostability of a fragment.

Adaptation of the electrophoretic methods described above to capillary electrophoresis allows faster throughput and more precision and sensitivity.

Heteroduplex analysis is useful for the detection of hyeterozygous SNPs, since these would form heteroduplexes and thus be readily detectable. This method has also been adapted to denaturing high-performance liquid chromatography (DHPLC). HPLC adds precision, speed and convenience; a typical run takes only 5 minutes to complete (Underhill et al. *Proc. Nat. Acad. Sci. USA*. USA. 93: 196–200 (1996). It has also been adapted to capillary electrophoresis (Righetti and Gelfi, Anal Biochem 244: 195–207 (1997).

Base excision sequence scanning (BESS) provides single base precision, requires no re-annealing of PCR fragments, prolonged optimization of a reaction step, or special gels or gel electrophoresis conditions. The BESS method works from the principle that 10 or 12 possible point mutations involve changes in deoxythymidine. Only G-->C and C--G transitions are excluded. Approximately 91% of these transitions could be detected by measuring changes on both strands of a DNA fragment. The overall single base pair (sbp) detection rate for BESS is >95%. (See Hawkins and Hoffman (1997) Nature Biotechnology, 15: 803–804; and Hawkins et al. 1997. Epicentre Forum, vol. 4, no. 2).

3. Direct sequencing.

A method for generating single-stranded DNA for use in DNA sequencing reactions is described in Gyllensten and Erlich, 1988, Proc. Natl. Acad. Sci. USA 85(20): 7652–7656, which is incorporated herein by reference. According to the method, unequal molar amounts of two amplification primers are employed to produce an excess of one strand of the PCR product.

Current cycle sequencing techniques are inherently incompatible with PCR amplification because they rely on the incorporation of chain terminators. By necessity, amplification must be performed prior to cycle sequencing. Porter et al (1997, *Nucleic Acids Res.* 25: 1611–1617) have described the use of boronated nucleotides to perform direct PCR sequencing without using chain truncators. Instead, the method relies upon digestion by an exonuclease to reveal the position of the digestion-resistant boranophosphate linkages. Thus, the sequencing fragments are derived directly from the original PCR products and the sequencing and amplification steps can be combined. Sequencing can be sued with or without allele specific analysis.

4. Allele specific technologies offer many advantages.

The cloning method used in example 1 is one such allele specific technology. The problems and advantages of cloning were examined carefully by Ennis, et al (Proc. Natl. Acad. Sci. USA 87, 2833–2837 (1995)).

Other allele specific technologies include various forms of allele-specific amplification. In general, allele-specific amplification requires a high degree of specificity of amplification and prior knowledge of suitable heterozygotic primer sites.

Heterozygotic primer sites can be identified by the screening methods described above. Only an approximate location is needed, so the low resolution methods described above and like methods would be sufficient. In particular, heteroduplex analysis would be convenient since it would directly reveal the location of heterozygotic sequences. With this information, allele-specific primers could be selected that would amplify specific alleles of the identified heterozygotic sequence.

In general, alternative procedures for enhanced specificity involve modified product detection procedures. For example, Saiki et al., 1986, Nature 324:163–166, describe a method for detecting allelic sequence variations due to single-base substitutions in human genomic DNA. The publication provides allele-specific oligonucleotide (ASO) probes that will only anneal to sequences that perfectly match the probe; a single mismatch being sufficient to prevent hybridization. The ASO probes are used in conjunction with amplification of a target segment containing an allelic sequence of According to the nested primer method of PCR, a second primer pair is designed to be internal to the first primer pair to amplify a subsegment of the first PCR product. The method increases specific amplification, i.e., reduces non-specific background amplification products and therefore increases sensitivity. Such non-specific amplification products, although they arise by virtue of fortuitous partial homology to the flanking primers, are unlikely to also have sufficient homology to the nested primers to continue to amplify. A homogeneous method of amplification using nested primers is described in U.S. Pat. No. 5,314,809 issued May 24, 1994 to Erlich and Higuchi.

Competitive oligonucleotide priming (COP), distinguishes closely related DNA sequences by comparing competitive annealing of two or more DNA sequences closely matched to the DNA sequence of interest.

Other procedures for allelic specific amplification include the TaqMan assay (Livak (1995) PCR Methods Appl. 4, 357–362; and U.S. Pat. No. 5,538,848 issued on Jul. 23, 1996 to Livak et al.). The TaqMan assay relies on allele-specific hybridization to remove the quenching of a fluorescent reporter by a FRET or analogous mechanism.

Tyagi et al (1996, *Proc. Nat. Acad. Sci. USA.*, 93: 5395–5400) have described a Q.β. RNA replicase-dependent amplification scheme that is unusual in that the probes, rather that the targets, are amplified exponentially. Signal generation, however, is strictly dependent on ligation of probes that have hybridized to the target molecules, no background signals are generated, and the resulting assays are extremely sensitive and specific. This method is capable of allele specific amplification.

Moreover, various methods can be combined to exploit the best characteristics of each. Delahunty, et al. (1996, Am. J. Hum. Genet. 58: 1239–1246), for example, have tested the feasibility of an SNP-based system for DNA identification. They utilized a combination of DNA amplification via PCR with the specificity of OLA to discriminate SNPs.

The Molecular Beacon assay (Tyagi and Kramer (1996) *Nat. Biotechnol.* 14, 303–308; and European Patent Application EP 0745690A2 issued to Tyagi et al) also offers allele-specific detection. Perfect complimentarity of the probe is required in both cases. The Molecular Beacon assay has the advantage that changes in fluorescence intensities can be monitored in real time. Both assays are one-step reactions, which makes them easy to set up. Nevertheless, they must be specifically optimized for the specific robe used. An apparatus designed for use with FRET-coupled labels as been described (U.S. Pat. No. 5,599,504, issued Feb. 4, 1997 to Shigeru et al.)

A recent procedure that would enhance detection of SNPs is artificial mismatch hybridization, described by Guo et al (1997, Nature Biotechnology, 15: 331–335). Artificial mismatch hybridization enhances discrimination of SNPs by using the base analog 3-nitropyrrole in probe oligonucleotides. It can be used to enhance discrimination either by binding of specific labeled probes or by binding of specific primers. In particular, it makes allele specific amplification feasible.

A survey of amplification systems was published in Bio/Technology 8:290–293, April 1990, incorporated herein by reference. In addition to PCR, the ligase chain reaction (LCR) is an alternative thermocycling amplification procedure. A combined PCR/LCR procedure is suitable for use in conjunction with the present invention. A brief summary of the ligation chain reaction is provided below for the convenience of those not familiar with ligation based amplification systems and to provide an understanding of the breadth of the present invention.

LCR is described in PCT Patent Publication No. Wo 89/09835, which is incorporated herein by reference. The process involves the use of ligase to join oligonucleotide segments that anneal to the target nucleic acid. LCR results in amplification of an original target molecule and can provide millions of copies of product DNA. Consequently, the LCR results in a net increase in double-stranded DNA.

Selective allelic amplification does not, by itself, provide a method to detect SNPs. The SNPs within amplified products must be detected. Detection systems that are useful for unanticipated polymorphisms include the following. These systems are useful for with or without allele-specific amplification. An automated sequence calling program, Polyphred, is said to be capable of calling heterozygous sequences with >99% accuracy (Nickerson et al., Nucleic Acids Research 25: 2745–2751 (1997)). Skilled persons would provide higher accuracy (Nickerson et al., Nucleic Acids Research 25: 2745–2751 (1997)).

One shortcoming of the amplification methods is the production of mutant sequences that result from misincorporation by the DNA polymerase used for amplification. The frequency of polymerase errors during PCR has been estimated. Using an error prone polymerase such as Taq DNA polymerase, the expected mutant frequency after 20 template doublings of a 1,000-bp sequence is about 40%. This problem is obviated to some extent with high fidelity polymerases such as Vent and Pfu polymerases, which in contrast to Taq possess editing exonuclease activity. However, inasmuch as the mutation frequency is a linear function of the size of the DNA segment, mutations produced by the latter polymerases become a problem when larger sequences are amplified. Modrich et al have developed a method for removal of polymerase-produced mutant sequences that arise during sequence amplification by PCR. After denaturation and reannealing, the PCR product pool is subjected to MutH, MutL, and MutS mismatch repair proteins under double-strand cleavage conditions, followed by identification of uncleaved product by size selection. The incidence of polymerase-induced mutant sequences within the uncleaved products is reduced ten-fold.

High-density DNA-chip arrays have been used for the simultaneous analysis of the entire human mitochondrial genome (Chee et al., Science (1996); 274: 610–614), and they would certainly be useful for analysis of the much smaller 950 base pair region of the present invention. For a recent review, see Southern, TIG 12: 110–115 (1996). Chee et al used a two color labeling scheme that allowed simultaneous comparison of a polymorphic target to a reference DNA (or RNA). SNPs were detected with great efficiency. The array was created using light-directed oligonucleotide array synthesis (see Pease et al., *Proc. Nat. Acad. Sci. USA.*, 91: 5022 (1994)). Any probe can be synthesized at any discrete, specified location in the array. Moreover, any set of probes can synthesized in a maximum of 4N cycles, where N is the length of the longest probe in the array. Strategy for the efficient design of arrays is described by Chee et al. For example, using a 4L tiled array, a nucleic acid target of length L can be scanned for mutations with a tiled array containing 4L probes.

Thus, to query 16, 569 base pairs of mitochondrial DNA required 66, 276 15-nucleotide oligomers.

Thus, to use the DNA-chip described above with the present technology would require only 4000 15-nucleotide oligomers for the entire 950 bp segment. The two-color labeling scheme could be used with the consensus sequence as a reference.

Another example of the application of DNA-chip technology is the chip for HIV enzyme sequence analysis that is available together with an instrument for its assay (Kreiner, Am. Lab. 28: 39–43 (1996). A further example is provided by Hacia et al (Nat. Genet. 14: 441–447 (1996), who used a high density oligonucleotide array to analyze a 3.45 kilobase BRCA1 exon. They used two-color analysis to detect heterozygous polymorphisms.

Other technologies have developed which further enhance the sensitivity and specificity of chip-based assays. See for example, Stimpson and Gordon (Genet Anal 13: 73–80 (1996), who describe the use of optical waveguide technology to detect DNA hybridization and melting within an array. The system is said to be amenable to detection of infrequent polymorphisms in the presence of an excess of the consensus, or wild type allele, provided the mutant sequence is present on the chip. Thus, it should readily detect heterozygotic sequences.

Nevertheless, for chip-based assays to determine complete haplotypes, it would be necessary to use allele specific amplification prior to analysis.

The use of peptide nucleic acid (PNA) hybridization for identification of nucleic acids is illustrated by Arlinghaus et al (Anal. Chem. 69: 3747–3753 (1997)). *Proc. Nat. Acad. Sci. USA.* are nucleic acid analogs in which the backbone consists of repeating units of N-(2-aminoethyl)glycine linked by amide bonds. The N-terminus corresponds to the 5' end of a DNA or RNA strand. The binding characteristics of PNA/DNA facilitate the detection of single-base mismatches. Moreover, the absence of phosphorus in PNA enables label-free detection of PNA/DNA complexes; the presence of phosphorus indicates that a complex has formed.

Another recently developed applicable technology is the detection of SNPs by competitive mobility shift assay, described by Chen et al. (Anal. Biochem. 239: 61069 (1996)). This assay is said to selectively detect SNPs in the presence of a large (up to one million-fold) excess of consensus or wild-type DNA.

Another recently developed applicable technology is the use of mass spectrometry for DNA sequencing. This subject is reviewed by Köster et al (Nature Biotechnology, 14: 113–1128.

Another recently developed applicable technology is the determination of SNPs by direct electric field control, described by Sosnowski et al (*Proc. Nat. Acad. Sci. USA.*, 94: 1119–1123 (1997)). This method is said to allow single base pair mismatch discrimination to be carried out rapidly and with high resolution.

An alternative to DNA-chip technology is offered by the use of a fiberoptic DNA sensor array capable of detecting SNPs. This technology is described by Healey et al (Anal. Biochem. 251: 270–279 (1997)). The sensitivity of this assay is said to be approximately 10-fold lower than previously reported DNA biosensors. The volume of the individual array elements is very small (20 pL), and thus is capable of application to a high-density array.

These scanning and screening techniques provide one skilled in the art with the means to detect new mutations within the DNA segment of the present invention without undue experimentation.

EQUIVALENTS

It will be appreciated that the methods and compositions of the present invention are capable of being incorporated in the form of a variety of embodiments, only a few of which have been illustrated and described above. While specific examples have been provided, the above description is illustrative and not restrictive. The invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within the scope of the invention.

All publications and patent documents cited in this application are incorporated by reference in their entirety for all purposes to the same extent as if each individual publication or patent document were so individually denoted.

What is claimed is:

1. A process for determining a discriminant function coefficient for ethnic affiliation, the process comprising:
   A. providing DNA samples from a plurality of human donors, the donors being of known ethnic groups; and
   B. isolating a region of DNA containing Alu U and Alu D from each sample, the region of DNA containing single-nucleotide polymorphisms, and the single-nucleotide polymorphisms being linked to form haplotypes;
   C. identifying a plurality of single-nucleotide polymorphisms present within the region of DNA by an effective means; and
   D. determining the frequency of each single-nucleotide polymorphism found within the region of DNA from the human donors; and
   E. estimating an expected haplotype frequency assuming random distribution of the single-nucleotide polymorphisms at the frequencies observed in step D; and
   F. determining the haplotypes present in each sample by an effective means; and
   G. associating the haplotype and the ethnic group of each donor; and
   H. summing the haplotypes associated with each ethnic group, thereby determining a specific group haplotype frequency; and
   I. calculating a discriminant function coefficient for each ethnic group by comparing the anticipated haplotype frequency to the specific group haplotype frequency.

2. The process of claim 1, wherein the region of DNA has a nucleotide diversity of at least 0.5%.

3. The process of claim 1, wherein the region of DNA contains Alu U.

4. The process of claim 1, wherein the region of DNa contains Alu D.

5. The method of claim 1, wherein the region of DNA is isolated by the process of:
   A. providing a restriction endonuclease that cleaves sequences flanking the region of DNA and that do not cleave within the region; and
   B. subjecting the DNA in each of the samples to the action of at least one restriction endonuclease that recognizes a cleavage site flanking the region of DNA to be isolated, thereby forming, in each of the two samples, a set of DNA fragments of a uniform size containing the region of DNA; and
   C. in each of the samples, separating by size the DNA fragments generated in step (B).

6. The method of claim 1, wherein the region of DNA is isolated by the process of:
   A. providing a set of primers capable of specifically supporting amplification of the region;
   B. subjecting the DNA to an amplification process primed by the set of primers of step (A).

7. A process of estimating ethnic affiliation, the process comprising:
   A. providing a DNA sample from a human, the sample containing DNA having Alu U and Alu D regions; and
   B. determining haplotypes within the Alu U and Alu D regions; and
   C. estimating the ethnic affiliation of the human from the discrimination coefficient for each ethnic group.

8. A process for determining an ethnic specific haplotype, the process comprising:
   A. providing DNA samples from a plurality of human donors, the donors being of known ethnic groups; and
   B. isolating a region of DNA containing Alu U and Alu D from each sample, the region of DNA containing single-nucleotide polymorphisms, and the single-nucleotide polymorphisms being linked to form haplotypes; and
   C. identifying a plurality of single-nucleotide polymorphisms present within the region of DNA by an effective means; and
   D. determining the haplotypes present in each sample by an effective means; and
   E. associating the haplotype and the ethnic group of each donor; and
   F. summing the haplotypes associated with each ethnic group, thereby determining a specific group haplotype frequency; and
   G. identifying haplotypes disproportionately associated with specific ethnic groups, thereby determining an ethnic specific haplotype.

9. A process for estimating genetic affiliation, the process comprising:
   A. providing DNA samples from a group of human donors; and
   B. isolating a region of DNA containing Alu U and Alu D from each sample;

C. subjecting the isolated regions to a procedure for detecting single-nucleotide polymorphisms; and D. determining the haplotypes present in each sample; and E. determining the distribution of the haplotypes within the group of human donors; and F. classifying the donors by haplotype; and G. estimating genetic affiliation by the disproportionate presence of a specific haplotype within a subset of the donors.

10. A method of forensic analysis comprising:

A. obtaining a first sample containing DNA from an individual human; and

B. obtaining a second sample containing a quantity of DNA sufficient for detection of a single-nucleotide polymorphism; and C. isolating a region of DNA containing Alu U and Alu D from the first sample;

D. isolating a region of DNA containing Alu U and Alu D from the second sample; and E. subjecting the isolated regions to a procedure for detecting single-nucleotide polymorphisms; and F. comparing the single nucleotide polymorphisms found in each sample, thereby analyzing the sample for forensic purposes.

* * * * *

SEQUENCE LISTING

<160> NUMBER OF SEQ ID NOS: 19

<210> SEQ ID NO 1
<211> LENGTH: 948
<212> TYPE: DNA
<213> ORGANISM: Artificial
<220> FEATURE:
<223> OTHER INFORMATION: HUMCON is a concensus sequence that reflects
      the predominant base at each location. The sequence includes 962
      possible positions, as shown in Table 1. Dashes are used in
      Table 1 to maintain alignment between the sequences.
<220> FEATURE:
<221> NAME/KEY: misc_feature
<222> LOCATION: (495)..(496)
<223> OTHER INFORMATION: n indicates g, c, t or a at that location.

<400> SEQUENCE: 1
tttcttggac ttcagggcag tttgctaggt ctgacctcct aaataaataa aaaaatatca      60
acataaagac tttatcccag aagtagacaa cgggtccgac ctcacgtcac cgagctagta     120
ccgagtgacg ttggaggtgg aggacccgag tccgctagga ggacggagtc ggagggttca     180
tcgaccctag tgtccgtgca cggtggcatg ggtcgactaa aaattgaaaa accaaaaaca     240
tctctaccct agagcgaaac aacgagtccg gaccagaggt tgaggacttg agttcactag     300
gtcgagtcgg agggtttcac gaccctaatg tccgcactcc gtggacacag accggtttaa     360
gtaaaaaatt ctctacccca gaatgataca acgggtccga cctttcgtca ccgtattagt     420
atcgagtgct gtcggagttt acggactcga gtttggtagg agggtggagt cggagcggta     480
cggaccggtc tccgnnaccc gacgactacg tggtacgtac caaaaaaaaa aaaaaaaaaa     540
aaaactctgc ctcagagcga gacagcgggt ccggtctgac gcctgacgtc accgcgttag     600
agccgagtga cgttcgaggc gaagggccca agtgtggtaa gaggacggag tcggagggct     660
catcgaccct gatgtccacg ggcggtggcg cgggccgatt aaaaaacata aaaatcatct     720
ctgccccaaa gtggaacaat cggtcctacc agagctagag gactggagta ctaggtgggc     780
ggagccggag ggtttcacga ccctaatgtc cgcactcggt gacgcgggcc ggagtggcac     840
gtacaaaatt tgtgtatggg tagttgctgt tctaacccct tcacttaccg aacctccgta     900
aacgtatctt caccttcgtg atccacccgc ctgtatttct gctgttac                948

<210> SEQ ID NO 2
<211> LENGTH: 951
<212> TYPE: DNA
<213> ORGANISM: Homo sapiens
<220> FEATURE:
<221> NAME/KEY: misc_feature
<222> LOCATION: (496)..(497)
<223> OTHER INFORMATION: n indicates g, c, t or a at that location.

<400> SEQUENCE: 2
tttcttggac ttcagggcag tttgctaggt ctgacctctt aaataaaaaa aaaaaatatc      60
aacataaaga ctttgtccca gaagtagaca acgggtccga cctcacgtca ccgagctagt     120

```
accgagtgac gttggaggtg gaggacccga gtccgctagg aggacggagt cggagggttc    180 atcgaccc ta gtgtccgtgc acggtggtat gggtcgacta aaaattgaaa actaaaaac    240 atctctaccc tagagcgaaa caacgagtcc ggaccagagg ttgaggactt gagttcacta    300
ggtcgagtcg gagggtttca cgaccctaat gtccgcactc cgtggacaca gaccggttta    360
agtaaaaaat tctctacccc agaatgatac aacgggtccg acctttcgtc accgtattag    420
tatcgagtgc tgtcggagtt tacggactcg agtttggtag gagggtggag tcggagcggt    480
acggaccggt ctccgnnacc cgacgactac gtggcacgta ccaaaaaaaa aaaaaaaaaa    540
aaaaactctg ctcaaagtcg agacagtaac agtgggtccg acctcgagtt atcgtgttag    600
agtcgagtga cattggagac ggaggaccca aggaattcgc taagaggacg gagtcggagg    660
gctcatcgac cctaatgtcg cgtacggtgg tgtgggccga ttgaaaacat agaaatcatt    720
tctgtctcaa agtggtacaa ccggtccgac cagagcttga ggcctggagt ccactaggcg    780
ggcggagccg gagggtttca cgaccctaat gtccgcactc ggtgacgcgg gccggagtgg    840
cacgtacaaa atttgcgtat gggtagttgc tgctctagcc ccttcactta ccgaacctcc    900
gtaaacgtat cttcaccttc gtgatccact cgcctgtatt tcttctgtta c             951
```

<210> SEQ ID NO 3
<211> LENGTH: 948
<212> TYPE: DNA
<213> ORGANISM: Homo sapiens
<220> FEATURE:
<221> NAME/KEY: misc_feature
<222> LOCATION: (494)..(496)
<223> OTHER INFORMATION: n indicates g, c, t or a at that location.

<400> SEQUENCE: 3

```
tttcttggac ttcagggcag tttgctaggt ctgacctcct aaataaataa aaaatatca     60 acataaagac tttatcccag aagtagacaa cgggtccgac ctcacgtcac cgagctagta    120
ccgagtgacg ttggaggtgg aggacccgag tccgctagga ggacggagtc ggagggttca    180
tcgaccctag tgtccgtgca cggtggcatg ggtcgactaa aaattgaaaa accaaaaaca    240
tctctaccct agagcgaaac aacgagtccg gaccagaggt tgaggacttg agttcactag    300
gtcgagtcgg agggtttcac gaccctaatg tccgcactcc gtggacacat accggtttaa    360
gtaaaaaatt ctctacccca gaatgataca acgggtccga cctttcgtca ccgtattagt    420
atcgagtgct gtcggagttc acggactcga gtttggtagg agggtggagt cggagcggta    480
cggaccggtc tccnnngccc gacgactacg tggtacgtac caaaaaaaaa aaaaaaaaaa    540
aaaactctgc ctcagatcga gacagcgggt ccggcctgac gcctgacgtc accgcgttag    600
agccgagtga cgttggaggc gaagggccca agtgtggtaa gaggacggag tcggagggct    660
catcgaccct gatgtccacg ggcggtggcg cgggccgatt aaaaaacata aaaatcatct    720
ctgccccaaa gtggaacaat cggtcctacc agagctagag gactggagta ctaggtgggc    780
ggaaccggag ggtttcacga ccctaatgtc cgcactcggt gacgcgggcc ggagtggcac    840
gtacaaaatt tgtgtatggg tagttgctgt tctaaccct tcacttaccg aacctccgta    900
aacgtatctt caccttcgtg atccaccgc ctgtatttct gctgttac                  948
```

<210> SEQ ID NO 4
<211> LENGTH: 943
<212> TYPE: DNA
<213> ORGANISM: Homo sapiens
<300> PUBLICATION INFORMATION:

-continued

```
<301> AUTHORS: Kass, D. H., M. A. Batzer, et al.
<302> TITLE: Gene conversion as a secondary mechanism of short
      interspersed element (SINE) evolution
<303> JOURNAL: Mol Cell Biol
<304> VOLUME: 15
<305> ISSUE: 1
<306> PAGES: 19-25
<307> DATE: 1995-01-06
<309> DATABASE ENTRY DATE:
<313> RELEVANT RESIDUES: (1)..(943)
<300> PUBLICATION INFORMATION:
<301> AUTHORS: Batzer, M. A., S. S. Arcot, et al.
<302> TITLE: Genetic variation of recent Alu insertions in human
      populations
<303> JOURNAL: J Mol Evol
<304> VOLUME: 42
<305> ISSUE: 1
<306> PAGES: 22-29
<307> DATE: 1996-01-07
<309> DATABASE ENTRY DATE:
<313> RELEVANT RESIDUES: (1)..(943)

<400> SEQUENCE: 4
tttcttggac ttcagggcag tttgctaggt ctgacctcct aaataaataa aaaaatatca      60
acataaagac tttatcccag aagtagacaa cgggtccgac ctcacgtcac cgagctagta     120
ccgagtgacg ttggaggtgg aggacccgag tccgctagga ggacggagtc ggagggttca     180
tcgaccctag tgtccgtgca cggtggcatg ggtcgactaa aaattgaaaa accaaaaaca     240
tctctaccct agagcgaaac aacgagtccg gaccagaggt tgaggacttg agttcactag     300
gtcgagtcgg agggtttcac gaccctaatg tccgcactcc gtggacacat accggtttaa     360
gtaaaaaatt ctctaccccca gaatgataca acgggtccga cctttcgtca ccgtattagt    420
atcgagtgct gtcggagttc acggactcga gtttggtagg agggtggagt cggagcggta    480
cggaccggtc tccggcccga cgactacgtg gtacgtacca aaaaaaaaaa aaaaaaaaa     540 aactctgcct cagagcgaga cagcgggtcc ggcctgacgc ctgacgtcac cgcgttagag    600
ccgagtgacg ttggaggcga agggcccaag tgtggtaaga ggacggagtc ggagggctca    660
tcgaccctga tgtccacggg cggtggcgcg ggccgattaa aaaacataaa aatctctgcc    720
ccaaagtgga acaatcggtc ctaccagagc tagaggactg gagtactagg tgggcggaac    780
cggagggttt cacgacccta atgtccgcac tcggtgacgc gggccggagt ggcacgtaca    840
aaatttgtgt atgggtagtt gctgttctaa ccccttcact taccgaacct ccgtaaacgt    900
atcttcacct tcgtgatcca cccgcctgta tttctgctgt tac                      943

<210> SEQ ID NO 5
<211> LENGTH: 942
<212> TYPE: DNA
<213> ORGANISM: Homo sapiens
<220> FEATURE:
<221> NAME/KEY: misc_feature
<222> LOCATION: (495)..(496)
<223> OTHER INFORMATION: n indicates g, c, t or a at that location.

<400> SEQUENCE: 5
tttcttggac ttcagggcag tttgctaggt ctgacctcct aaataaataa aaaaatatca      60
acataaagac tttatcccag aagtagacaa cgggtccgac ctcacgtcac cgagctagta     120
ccgagtgacg ttggaggtgg aggacccgag tccgctagga ggacggagtc ggagggttca     180
tcgaccctag tgtccgtgca cggtggcatg ggtcgactaa aaattgaaaa accaaaaaca     240
tctctaccct agagcgaaac aacgagtccg gaccagaggt tgaggacttg agttcactag     300
gtcgagtcgg agggtttcac gaccctaatg tccgcactcc gtggacgcat accggtttaa     360
```

```
gtaaaaaatt ctctacccca gaatgataca acgggtccga cctttcgtca ccgtattagt    420
atcgagtgct gtcggagttc acggactcga gtttggtagg aggtggagt cggagcggta     480 cggaccggtc tccgnnaccc gacgactacg tggtacgtac caaaaaaaaa aaaaaaaaaa    540
actctgcctc agagcgagac agcgggtccg gcctgacgcc tgacgtcacc gcgttagagc    600
cgagtgacgt tggaggcgaa gggcccaagt gtggtaagag gacggagtcg gagggctcat    660
cgaccctgat gtccacgggt ggtggcgcgg gccgattaaa aaacataaaa atctctgccc    720
caaagtggaa caatcggtcc taccagagct agaggactgg agtactaggt gggcggaacc    780
ggagggtttc acgaccctaa tgtccgcact cggtgacgcg ggccggagtg gcacgtacaa    840
aatttgtgta tgggtagttg ctgttctaac cccttcactt accgaacctc cgtaaacgta    900
tcttcacctt cgtgatccac ccgcctgtat ttctgctgtt ac                      942

<210> SEQ ID NO 6
<211> LENGTH: 948
<212> TYPE: DNA
<213> ORGANISM: Homo sapiens
<220> FEATURE:
<221> NAME/KEY: misc_feature
<222> LOCATION: (494)..(496)
<223> OTHER INFORMATION: n indicates g, c, t or a at that location.

<400> SEQUENCE: 6
tttcttggac ttcagggcag tttgctaggt ctgacctcct aaataaataa aaaaatatca     60
acataaagac tttatcccag aagtagacaa cgggtccgac ctcacgtcac cgagctagta    120
ccgagtgacg ttgaggtgg aggacccgag tccgctagga ggacggagtc ggagggttca    180
tcgaccctag tgtccgtgca cggtggtatg ggtcgactaa aaattgaaaa accaaaaaca    240
tctctaccct agagcgaaac aacgagtccg gaccagaggt tgaggacttg agttcactag    300
gtcgagtcgg agggtttcac gaccctaatg tccgcactcc gtggacacag accggtttaa    360
gtaaaaaatt ctctacccca gaatgataca acgggtccga cctttcgtca ccgtattagt    420
atcgagtgct gtcggagttt acggactcga gtttggtagg agggtggagt cggagcggta    480
cggaccggtc tccnnnaccc gacgactacg tggtacgtac caaaaaaaaa caaaaaaaaa    540
aaaactctgc ctcagagcga gacagcgggt ccggtctgac gcctgacgtc accgcgttag    600
agccgagtga cgttcgaggc gaagggccca agtgtggtaa gaggacggag tcggagggct    660
catcgaccct gatgtccacg ggtggtggcg cgggccgatt aaaaaacata aaatcatct    720 ctgccccaaa gtggaacaat cggtcctacc agagctagag gactggagta ctaggtgggc    780
ggagccggag ggtttcacga ccctaatgtc cgcactcggt gacgcgggcc ggagtggcac    840
gtacaaaatt tgtgtatggg tagttgctgt tctaacccct tcacttaccg aacctccgta    900
aacgtatctt caccttcgtg atccacccgc ctgtatttct gctgttac                948

<210> SEQ ID NO 7
<211> LENGTH: 948
<212> TYPE: DNA
<213> ORGANISM: Homo sapiens

<400> SEQUENCE: 7
tttcttggac ttcagggcag tttgctaggt ctgacctcct aaataaataa aaaaatatca     60
acataaagac tttatcccag aagtagacaa cgggtccgac ctcacgtcac cgagctagta    120
ccgagtgacg ttgaggtgg aggacccgag tccgctagga ggacggagtc ggagggttca    180
```

-continued

```
tcgaccctag tgtccgtgca cggtggtatg ggtcgactaa aaattgaaaa accaaaaaca      240
tctctaccct agagcgaaac aacgagtccg gaccagaggt tgaggacttg agttcactag      300
gtcgagtcgg agggtttcac gaccctaatg tccgcactcc gtggacacag accggtttaa      360
gtaaaaaatt ctctacccca gaatgataca acgggtccga cctttcgtca ccgtattagt      420
atcgagtgct gtcggagttt acggactcga atttggtagg agggtggagt cggagcggta      480
cggaccggtc tccggtaccc gacgactacg tggtacgtac caaaaaaaaa caaaaaaaaa      540
aaaactctgc ctcagagcga gacagcgggt ccggtctgac gcctgacgtc accgcgttag      600
agccgagtga cgttcgaggc gaagggccca agtgtggtaa gaggacggag tcggagggct      660
catcgaccct gatgtccacg ggcggtggcg cgggccgatt aaaaaacata aaaatcatct      720
ctgccccaaa gtgcaacaat cggtcctacc agagctagag gactggagta ctaggtgggc      780
ggagccggag ggtttcacga ccctaatgtc cgcactcggt gacgcgggcc ggagtggcac      840
gtacaaaatt tgtgtatggg tagttgctgt tctaacccct tcacttaccg aacctccgta      900
aacgtatctt caccttcgtg atccacccgc ctgtatttct gctgttac                  948
```

<210> SEQ ID NO 8
<211> LENGTH: 950
<212> TYPE: DNA
<213> ORGANISM: Homo sapiens

<400> SEQUENCE: 8

```
tttcttggac ttcagggcag tttgctaggt ctgacctcct aaataaataa aaaaaatatc       60
aacataaaga ctttatccca gaagtagaca acgggtccga cctcacgtca ccgagctagt      120
accgagtgac gttggaggtg gaggacccga gtccgctagg aggacggagt cggagggttc      180
atcgacccta gtgtccgtgc acggtggtat gggtcgacta aaaattgaaa accaaaaaac      240
atctctaccc tagagcgaaa caacgagtcc ggaccagagg ttgaggactt gagttcacta      300
ggtcgagtcg gagggtttca cgaccctaat gtccgcactc cgtggacaca gaccggttta      360
agtaaaaaat tctctacccc agaatgatac aacgggtccg acctttcgtc accgtattag      420
tatcgagtgc tgtcggagtt tacggactcg agtttggtag gagggtggag tcggagcggt      480
acggaccggt ctccggtacc cgacgactac gtggtacgta ccaaaaaaaa acaaaacaaa      540
aaaaactctg cctcagagcg agacagcggg tccggtctga cgcctgacgt caccgcgtta      600
gagccgagtg acgttgaagg cgaagggccc aagtgtggta agaggacgga gtcggagggc      660
tcatcgaccc tgatgtccac gggtggtggc gcgggccgat taaaaaacat aaaaatcatc      720
tctgccccaa gtggaacaa tcggtcctac cagagctaga ggactggagt actaggtggg      780
cggagccgga gggtttcacg accctaatgt ccgcactccg gtgacgcggg ccggagtggc      840
acgtacaaaa tttgtgtatg ggtagttgct gttctaaccc cttcacttac cgaacctccg      900
taaacgtatc ttcaccttcg tgatccaccc acctgtattt ctgctgttac                 950
```

<210> SEQ ID NO 9
<211> LENGTH: 945
<212> TYPE: DNA
<213> ORGANISM: Homo sapiens
<220> FEATURE:
<221> NAME/KEY: misc_feature
<222> LOCATION: (494)..(495)
<223> OTHER INFORMATION: n indicates g, c, t or a at that location.

<400> SEQUENCE: 9

```
tttcttggac ttcagggcag tttgctaggt ctgacctcct aataaataag aaaatatcaa       60
```

```
cataaagact ttatcccaga agtagacaac gggtccgacc tcacgtcacc gagctagtac    120
cgagtgacgt tggaggtgga ggacccgagt ccgctaggag gacggagtcg gagggttcat    180
cgaccctagt gtccgtgcac ggtggtatgg gtcgactaaa aattgaaaaa ccaaaaacat    240
ctctacccta gagcgaaaca acgagtccgg accagaggtt gaggacttga gttcactagg    300
tcgagtcgga gggtttcacg accctaatgt ccgcactccg tggacacaga ccggtttaag    360
taaaaaattc tctaccccag aatgatacaa cgggtccgac ctttcgtcac cgtattagta    420
tcgagtgctg tcggagttta cggactcgag tttggtagga gggtggagtc ggagcggtac    480
ggaccggtct ccgnnacccg acgactacg ggtacgtacc aaaaaaaaca aaaaaaaaa     540 actctgcctc agagcgagac agcgggtccg gtctgacgcc tgacgtcacc gcgttagagc    600
cgagtgacgt tcgaggcgaa gggcccaagt gtggtaagag gacggagtcg gagggctcat    660
cgaccctgat gtccacgggc ggtggtgcgg gccgattaaa aaacataaaa atcatctctg    720
ccccaaagtg aacaatcggt cctaccagag ctagaggact ggagtactag gtgggcggag    780
ccggaggggt tcacgaccct aatgtccgca ctccggtgac gcgggccgga gtggcacgta    840
caaaatttgt gtatgggtag ttgctgttct aacccttca cttaccgaac ctccgtaaac    900
gtatcttcac cttcgtgatc cacccgcctg tatttctgct gttac                   945

<210> SEQ ID NO 10
<211> LENGTH: 948
<212> TYPE: DNA
<213> ORGANISM: Homo sapiens
<220> FEATURE:
<221> NAME/KEY: misc_feature
<222> LOCATION: (495)..(496)
<223> OTHER INFORMATION: n indicates g, c, t or a at that location.

<400> SEQUENCE: 10
tttcttggac ttcagggcag tttgctaggt ctgacctcct aaataaataa aaaaatatca     60
acataaagac tttatcccag aagtagacaa cgggtccgac ctcacgtcac cgagctagta    120
ccgagtgacg ttggaggtgg aggacccgag tccgctagga ggacggagcc ggagggttca    180
tcgaccctag tgtccgtgca cggtggcatg ggtcgactaa aaattgaaaa accaaaaaca    240 tctctacccct agagcgaaac aacgagtccg gaccagaggt tgaggacttg agttcactag    300
gtcgagtcgg agggtttcac gaccctaatg tccgcactcc gtggacacag accggtttaa    360
gtaaaaaatt ctctaccccca gaatgataca acgggtccga cctttcgtca ccgtattagt    420
atcgagtgct gtcggagttt acggactcga gtttggtagg aggtggagt cggagcggta    480 cggaccggtc tccgnnaccc gacgactacg tggtacgtac caaaaaaaa caaaaaaaa    540 aaactctgcc tcagagcgag acagcgggtc cggtctgacg cctgacgtca ccgcgttaga    600
gccgagtgac gttcgaggcg aagggcccaa gtgtggtaag aggacggagt cggagggctc    660
atcgaccctg atgttcacgg gtggtggcgc gggccgatta aaaaacataa aaatcatctc    720
tgccccaaag tggaacaatc ggtcctacca gagctagagg actggagtac taggtgggcg    780
gagccggagg gtttcacgac cctaatgtcc gcactccggt gacgcgggcc ggagtggcac    840
gtacaaaatt tgtgtatggg tagttgctgt tctaacccct tcacttaccg aacctccgta    900
aacgtatctt caccttcgtg atccacccgc ctgtatttct gctgttac                 948

<210> SEQ ID NO 11
<211> LENGTH: 947
<212> TYPE: DNA
```

<213> ORGANISM: Homo sapiens
<220> FEATURE:
<221> NAME/KEY: misc_feature
<222> LOCATION: (614)..(615)
<223> OTHER INFORMATION: n indicates g, c, t or a at that location.

<400> SEQUENCE: 11

| | | | | | |
|---|---|---|---|---|---|
| tttcttggac | ttcagggcag | tttgctaggt | ctgacctcct | aaataaataa | aaaaatatca | 60 |
| acataaagac | tttatcccag | aagtagacaa | cgggtccgac | ctcacgtcac | cgagctagta | 120 |
| ccgagtgacg | ttggaggtgg | aggacccgag | tccgctagga | ggacggagtc | ggagggttca | 180 |
| tcgaccctag | tgtccgtgca | cggtggtatg | ggtcgactaa | aaattgaaaa | accaaaaaca | 240 |
| tctctaccct | agagcgaaac | aacgagtccg | gaccagaggt | tgaggacttg | agttcactag | 300 |
| gtcgagtcgg | agggtttcac | gaccctaatg | tccgcactcc | gtggacacag | accggtttaa | 360 |
| gtaaaaaatt | ctctaccccca | gaatgataca | acgggtccga | cctttcgtca | ccgtattagt | 420 |
| atcgagtgct | gtcggagttt | acggactcga | gtttggtagg | agggtggagt | cggagcggta | 480 |
| cggaccggtc | tccggtaccc | gacgactacg | tggtacgtac | caaaaaaaaa | caaaaaaaaa | 540 |
| aaactctgcc | tcagagcgag | acagcgggtc | cggtctgacg | cctgacgtca | ccgcgttaga | 600 |
| gccgagtgac | gttnnaggcg | aagggcccaa | gtgtggtaag | aggacggagt | cggagggctc | 660 |
| atcgaccctg | atgtccacgg | gtggtggcgc | gggccgatta | aaaaacataa | aaatcatctc | 720 |
| tgccccaaag | tggaacaatc | ggtcctacca | gagctagagg | actggagtac | taggtgggcg | 780 |
| gagccggagg | gtttcacgac | cctaatgtcc | gcactcggtg | acgcgggccg | gagtggcacg | 840 |
| tacaaaattt | gtgtatgggt | agttgctgtt | ctaaccccctt | cacttaccga | acctccgtaa | 900 |
| acgtatcttc | accttcgtga | tccacccgcc | tgtatttctg | ctgttac | | 947 |

<210> SEQ ID NO 12
<211> LENGTH: 947
<212> TYPE: DNA
<213> ORGANISM: Homo sapiens

<400> SEQUENCE: 12

| | | | | | |
|---|---|---|---|---|---|
| tttcttggac | ttcagggcag | tttgctaggt | ctgacctcct | aaataaataa | aaaaatatca | 60 |
| acataaagac | tttatcccag | aagtagacaa | cgggtccgac | ctcacgtcac | cgagctagta | 120 |
| ccgagtgacg | ttggaggtgg | aggacccgag | tccgctagga | ggacggagtc | ggagggttca | 180 |
| tcgaccctag | tgtccgtgca | cggtggcatg | ggtcgactaa | aaattgaaaa | accaaaaaca | 240 |
| tctctaccct | agagcgaaac | aacgagtccg | gaccagaggt | tgaggacttg | agttcactag | 300 |
| gtcgagtcgg | agggtttcac | gaccctaatg | tccgcactcc | gtggacacag | accggtttaa | 360 |
| gtaaaaaatt | ctctaccccca | gaatgataca | acgggtccga | cctttcgtca | ccgtattagt | 420 |
| atcgagtgct | gtcggagttt | acggactcga | gtttggtagg | agggtggagt | cggagcggta | 480 |
| cggaccggtc | tccggtaccc | gacgactacg | tggtacgtac | caaaaaaaaa | caaaaaaaaa | 540 |
| aaaactctgc | ctcagagcga | gacagcgggt | ccggtctgac | gcctgacgtc | accgcgctag | 600 |
| agccgagtga | cgttcgaggc | gaagggccca | agtgtggtaa | gaggacggag | tcggagggct | 660 |
| catcgaccct | gatgtccacg | ggtggtggcg | cgggccgatt | aaaaaacata | aaatcatctc | 720 |
| tgccccaaaa | gtgcacaatc | ggtcctacca | gagctagagg | actggagtac | taggtgggcg | 780 |
| gagccggagg | gtttcacgac | cctaatgtcc | gcactcggtg | acgcgggccg | gagtggcacg | 840 |
| tacaaaattt | gtgtatgggt | agttgctgtt | ctaaccccctt | cacttaccga | acctccgtaa | 900 |
| acgtatcttc | accttcgtga | tccacccgcc | tgtatttctg | ctgttac | | 947 |

<210> SEQ ID NO 13
<211> LENGTH: 948
<212> TYPE: DNA
<213> ORGANISM: Homo sapiens
<220> FEATURE:
<221> NAME/KEY: misc_feature
<222> LOCATION: (615)..(616)
<223> OTHER INFORMATION: n indicates g, c, t or a at that location.

<400> SEQUENCE: 13

| | | | | | | |
|---|---|---|---|---|---|---|
| tttcttggac | ttcagggcag | tttgctaggt | ctgacctcct | aaataaataa | aaaatatca | 60 |
| acataaagac | tttatcccag | aagtagacaa | cgggtccgac | ctcacgtcac | cgagctagta | 120 |
| ccgagtgacg | ttggaggtgg | aggacccgag | tccgctagga | ggacggagtc | ggagggttca | 180 |
| tcgaccctag | tgtccgtgca | cggtggtatg | ggtcgactaa | aaattgaaaa | accaaaaaca | 240 |
| tctctaccct | agagcgaaac | aacgagtccg | gaccagaggt | tgaggacttg | agttcactag | 300 |
| gtcgagtcgg | agggtttcac | gaccctaatg | tccgcactcc | gtggacacag | accggtttaa | 360 |
| gtaaaaaatt | ctctacccca | gaatgataca | acgggtccga | cctttcgtca | ccgtattagt | 420 |
| atcgagtgct | gtcggagttt | acggactcga | gtttggtagg | agggtggagt | cggagcggta | 480 |
| cggaccggtc | tccggtaccc | gacgactacg | tggtacgtac | caaaaaaaaa | caaaaaaaaa | 540 |
| aaaactctgc | ctcagagcga | gacagcgggt | ccggtctgac | gcctgacgtc | accgcgttag | 600 |
| agccgagtga | cgttnnaggc | gaagggccca | agtgtggtaa | gaggacggag | tcggagggct | 660 |
| catcgaccct | gatgtccacg | ggtggtggcg | cgggccgatt | aaaaaacata | aaatcatct | 720 |
| ctgccccaaa | gtggaacaat | cggtcctacc | agagctagag | gactggagta | ctaggtgggc | 780 |
| ggagccggag | ggtttcacga | ccctaatgtc | cgcactcggt | gacgcgggcc | ggagtggcac | 840 |
| gtacaaaatt | tgtgtatggg | tagttgctgt | tctaacccct | tcacttaccg | aacctccgta | 900 |
| aacgtatctt | caccttcgtg | atccacccgc | ctgtatttct | gctgttac | | 948 |

<210> SEQ ID NO 14
<211> LENGTH: 948
<212> TYPE: DNA
<213> ORGANISM: Homo sapiens
<220> FEATURE:
<221> NAME/KEY: misc_feature
<222> LOCATION: (615)..(616)
<223> OTHER INFORMATION: n indicates g, c, t or a at that location.

<400> SEQUENCE: 14

| | | | | | | |
|---|---|---|---|---|---|---|
| tttcttggac | ttcagggcag | tttgctaggt | ctgacctcct | aaataaataa | aaaatatca | 60 |
| acataaagac | tttatcccag | aagtagacaa | cgggtccgac | ctcacgtcac | cgagctagta | 120 |
| ccgagtgacg | ttggaggtgg | aggacccgag | tccgctagga | ggacggagtc | ggagggttca | 180 |
| tcgaccctag | tgtccgtgca | cggtggtatg | ggtcgactaa | aaattgaaaa | accaaaaaca | 240 |
| tctctaccct | agagcgaaac | aacgagtccg | gaccagaggt | tgaggacttg | agttcactag | 300 |
| gtcgagtcgg | agggtttcac | gaccctaatg | tccgcactcc | gtggacacag | accggtttaa | 360 |
| gtaaaaaatt | ctctacccca | gaatgataca | acgggtccga | cctttcgtca | ccgtattagt | 420 |
| atcgagtgct | gtcggagttt | acggactcga | gtttggtagg | agggtggagt | cggagcggta | 480 |
| cggaccggtc | tccggtaccc | gacgactacg | tggtacgtac | caaaaaaaaa | caaaaaaaaa | 540 |
| aaaactctgc | ctcagagcga | gacagcgggt | ccggtctgac | gcctgacgtc | accgcgttag | 600 |
| agccgagtga | cgttnnaggc | gaagggccca | agtgtggtaa | gaggacggag | tcggagggct | 660 |

-continued

```
catcgaccct gatgtccacg ggtggtggcg cgggccgatt aaaaaacata aaaatcatct    720
ctgccccaaa gtggaacaat cggtcctacc agagctagag gactggagta ctaggtgggc    780
ggagccggag ggtttcacga ccctaatgtc cgcactcggt gacgcgggcc ggagtggcac    840
gtacaaaatt tgtgtatggg tagttgctgt tctaacccct tcacttaccg aacctccgta    900
aacgtatctt caccttcgtg atccacccgc ctgtatttct gctgttac                948
```

<210> SEQ ID NO 15
<211> LENGTH: 950
<212> TYPE: DNA
<213> ORGANISM: Homo sapiens

<400> SEQUENCE: 15

```
tttcttggac ttcagggcag tttgctaggt ctgacctcct aaataaataa aaaaaatatc     60
aacataaaga ctttatccca gaagtagaca acgggtccga cctcacgtca ccgagctagt    120
accgagtgac gttggaggtg gaggacccga gtccgctagg aggacggagt cggagggttc    180 atcgaccta gtgtccgtgc acggtggtat gggtcgacta aaaattgaaa aaccaaaaac    240
atctctaccc tagagcgaaa caacgagtcc ggaccagagg ttgaggactt gagttcacta    300
ggtcgagtcg gagggtttca cgaccctaat gtccgcactc cgtggacaca gaccggttta    360
agtaaaaaat tctctacccc agaatgatac aacgggtccg acctttcgtc accgtattag    420
tatcgagtgc tgtcggagtt tacggactcg agtttggtag gagggtggag tcggagcggt    480
acggaccggt ctccggtacc cgacgactac gtggtacgta ccaaaaaaaa acaaaacaaa    540
aaaaactctg cctcagagcg agacagcggg tccggtctga cgcctgacgt caccgcgtta    600
gagccgagtg acgttcgagg cgaagggccc aagtgtggta agaggacgga gtcggagggc    660
tcatcgaccc tgatgtccac gggtggtggc gcgggccgat taaaaaacat aaaaatcatc    720
tctgccccaa gtggaacaa tcggtcctac cagagctaga ggactggagt actaggtggg    780
cggagccgga gggtttcacg accctaatgt ccgcactccg gtgacgcggg ccggagtggc    840
acgtacaaaa tttgtgtatg ggtagttgct gttctaaccc cttcacttac cgaacctccg    900
taaacgtatc ttcaccttcg tgatccaccc gcctgtattt ctgctgttac                950
```

<210> SEQ ID NO 16
<211> LENGTH: 21
<212> TYPE: DNA
<213> ORGANISM: Artificial
<220> FEATURE:
<223> OTHER INFORMATION: Forward external primer for LDLR sequence.

<400> SEQUENCE: 16

```
agtgctagtg ccgaaacttc a                                               21
```

<210> SEQ ID NO 17
<211> LENGTH: 21
<212> TYPE: DNA
<213> ORGANISM: Artificial
<220> FEATURE:
<223> OTHER INFORMATION: Reverse external primer for LDLR sequence.

<400> SEQUENCE: 17

```
ttagcggcac aatgacaacg t                                               21
```

<210> SEQ ID NO 18
<211> LENGTH: 23
<212> TYPE: DNA
<213> ORGANISM: Artificial

-continued

```
<220> FEATURE:
<223> OTHER INFORMATION: Internal primer for LDLR sequence.

<400> SEQUENCE: 18
tcacgaccct aatgtccgca ctc                                            23

<210> SEQ ID NO 19
<211> LENGTH: 21
<212> TYPE: DNA
<213> ORGANISM: Artificial
<220> FEATURE:
<223> OTHER INFORMATION: Internal primer for LDLR sequence.

<400> SEQUENCE: 19
acgactacgt ggtacgtacc a                                              21
```